United States Patent [19]

Kochinke et al.

[11] Patent Number: 5,613,958
[45] Date of Patent: Mar. 25, 1997

[54] TRANSDERMAL DELIVERY SYSTEMS FOR THE MODULATED ADMINISTRATION OF DRUGS

[75] Inventors: Frank Kochinke, San Jose; William R. Pfister, Union City; Jenny Louie, Fremont; Dan Arenson, Escondido, all of Calif.

[73] Assignee: PP Holdings Inc., Menlo Park, Calif.

[21] Appl. No.: 469,178

[22] Filed: Jun. 6, 1995

Related U.S. Application Data

[63] Continuation-in-part of Ser. No. 60,907, May 12, 1993, abandoned.

[51] Int. Cl.$^6$ ........................................... A61F 13/02
[52] U.S. Cl. .................. 604/307; 604/890.1; 602/52; 602/54; 602/58; 424/449; 514/947
[58] Field of Search ..................... 604/304, 307, 604/890.1, 891.1, 892.1; 602/41–42, 48, 52, 54–55, 58; 424/448, 449; 514/946–947

[56] References Cited

U.S. PATENT DOCUMENTS

| | | |
|---|---|---|
| 3,532,708 | 10/1970 | Balance . |
| 3,742,951 | 7/1973 | Zaffaroni . |
| 4,420,470 | 12/1983 | Otsuka et al. . |
| 4,559,222 | 12/1985 | Enscore et al. . |
| 4,624,665 | 11/1986 | Nuwayser ............................ 604/307 |

(List continued on next page.)

FOREIGN PATENT DOCUMENTS

| | | |
|---|---|---|
| 1207236 | 7/1986 | Canada . |
| 2039869 | 7/1991 | Canada . |
| 2062828 | 10/1991 | Canada . |
| 325843 | 8/1989 | European Pat. Off. . |
| 344820 | 12/1989 | European Pat. Off. . |

(List continued on next page.)

OTHER PUBLICATIONS

Morimoto, Y.; Hatanaka, T.; et al. "A screening method for percutaneous absorption enhancers appropriate for adhesive matirix devices," *S.T.P. Pharma Sciences*, 1992, 2(3) 253–258.

Wagner, F.; Siefert, F.; et al. "Relationship between pharmacokinetics and hemodynamic tolerance to isosorbide–5–mononitrate," *European Journal of Clinical Pharmacology*, 1990, S53–S59.

(List continued on next page.)

*Primary Examiner*—John G. Weiss
*Assistant Examiner*—P. Zuttarelli
*Attorney, Agent, or Firm*—Townsend and Townsend and Crew

[57] ABSTRACT

A transdermal delivery system for the modulated administration of drugs is described. The drug delivery device comprises a backing; a drug reservoir containing the drug, a plasticizer-type enhancer, a solvent-type enhancer, and optionally, a gelling agent; a non-rate-controlling membrane; and an adhesive layer containing a plasticizer-type enhancer. This drug delivery system is particularly useful for the administration of tolerance-inducing drugs, for example, vasodilators, such as isosorbide dinitrate.

44 Claims, 10 Drawing Sheets

Modulated delivery profile for transdermal administration of tolerance producing drugs; where X is between 2 and 10 hours, y is approximately 8 to 18 hours and z is approximately 24 hours at which point the transdermal patch is removed.

U.S. PATENT DOCUMENTS

| | | |
|---|---|---|
| 4,698,062 | 10/1987 | Gale et al. . |
| 4,704,119 | 11/1987 | Shaw et al. . |
| 4,711,781 | 12/1987 | Nick et al. .............................. 424/446 |
| 4,725,272 | 2/1988 | Gale . |
| 4,746,509 | 5/1988 | Haggiage et al. . |
| 4,758,434 | 7/1988 | Kydonieus et al. . |
| 4,767,808 | 8/1988 | Kydonieus et al. . |
| 4,784,856 | 11/1988 | Fukuda et al. . |
| 4,804,541 | 2/1989 | Nichols . |
| 4,820,720 | 4/1989 | Sanders et al. . |
| 4,846,826 | 7/1989 | Shaw et al. . |
| 4,885,174 | 12/1989 | Bodor et al. . |
| 4,927,408 | 5/1990 | Haak et al. . |
| 4,938,759 | 7/1990 | Enscore et al. . |
| 4,956,181 | 9/1990 | Bayer et al. . |
| 5,023,082 | 6/1991 | Friedman et al. ..................... 424/426 |
| 5,064,654 | 11/1991 | Berner et al. . |
| 5,071,656 | 12/1991 | Lee et al. . |
| 5,164,189 | 11/1992 | Farhadieh et al. . |
| 5,164,416 | 11/1992 | Nagai et al. . |
| 5,176,916 | 1/1993 | Yamanaka et al. . |

FOREIGN PATENT DOCUMENTS

| | | |
|---|---|---|
| 436203 | 7/1991 | European Pat. Off. . |
| 68090 | 6/1986 | Israel . |
| 60169414 | 9/1985 | Japan . |
| 3-063233 | 3/1991 | Japan . |
| 3-123727 | 5/1991 | Japan . |
| 0429927 | 1/1992 | Japan . |
| 0413617 | 1/1992 | Japan . |
| 4095024 | 3/1992 | Japan . |
| 2100605 | 1/1983 | United Kingdom ................. 604/307 |
| WO86/00814 | 2/1986 | WIPO . |
| WO91/02506 | 3/1991 | WIPO . |
| WO91/02553 | 3/1991 | WIPO . |
| WO91/03998 | 4/1991 | WIPO . |
| WO91/16044 | 10/1991 | WIPO . |
| WO92/10154 | 6/1992 | WIPO . |

OTHER PUBLICATIONS

Barton, A.F.M. *CRC Handbook of Solubility Parameters and Other Cohesion Parameters,* CRC Press, Inc., Boca Raton, Florida, 1983.

"Nitroglycerin Patches—Circumventing Problems of Tolerance," *American Pharmacy,* 1987, vol. NS27 (No. 1), 18–20.

Asmussen, Bodo "Transdermal Therapeutic Systems—Actual State and Future Developments," *Meth. Find. Exp. Clin. Pharmacol.,* 1991, 13(5): 343–351.

Hansen, Laila B.; Fullerton, Ann; et al. "Enhanced transdermal delivery of ketobemidone with prodrugs," *International Journal of Pharmaceutics,* 1992, 84, 253–260.

Pfister, William R.; Hsieh, Dean S.T. "Permeation Enhancers Compatible with Transdermal Drug Delivery Systems, Part I: Selection and Formulation Considerations," *Phar. Tech. Int.,* 1991, 3(1):32–36.

Pfister, William R.; Hsieh, Dean S.T. "Permeation Enhancers Compatible with Transdermal Drug Delivery Systems, Part II: System Design Considerations", *Phar. Tech. Int.,* 1991, 3(2): 28–32.

Agabeyoglu, I.T.; Ocak, F. "Isosorbide Dinitrate Releasing Transdermal Drug Delivery: Dissolution Rate Studies and Release Kinetics II", *Proceed. Intern. Symp. Control Rel. Bioact. Mater.,* 1992, 19, Controlled Release Society, Inc., #1324, 493–494.

"*Test Methods for Pressure Sensitive Tapes*", Pressure Sensitive Tape Council, Ninth Edition.

Seki, T.; Kawaguchi, T.; Sugibayashi, K.; Juni, K.; Morimoto, Y. "Membrane Permeation–Controlled Transdermal Delivery System Design. Influence of Controlling Membrane and Adhesive on Skin Permation of Isosorbide Dinitrate", *Chem. Pharm Bull.,* 1990, (Tokyo), 38, 740–743.

Yukawa, J.; Sugibayashi, K.; Morimoto, Y. "Effect of Various Additives on the Skin Permation of Ketoprofen from the Film Forming Transdermal Formulation", *Yakuzaigaku,* 1989, 49, 252–254.

Agabeyoglu, et al., "Isosorbide Dinitrate Releasing Transdermal Drug Delivery: Dissolution Rate Studies and Release Kinetics II.," *Proceed. Intern. Symp. Control. Rel. Bioact. Mater.,* 19 (1992) pp. 493–393, Controlled Release Society, Inc.

Modulated delivery profile for transdermal administration of tolerance producing drugs; where $x$ is between 2 and 10 hours, $y$ is approximately 8 to 18 hours and $z$ is approximately 24 hours at which point the transdermal patch is removed.

TRANSDERMAL DELIVERY SYSTEMS FOR THE MODULATED ADMINISTRATION OF DRUGS

This application is a continuation-in-part of patent application Ser. No. 08/060,907 filed May 12, 1993 now abandoned.

BACKGROUND OF THE INVENTION

1. Field of the Invention

This invention relates to the transdermal delivery of drugs. More specifically, a transdermal drug delivery system is utilized to deliver a therapeutically effective amount of a drug, via a modulated drug delivery profile, through the skin of a patient in need of such treatment. This device is particularly suitable for the delivery of tolerance-inducing drugs.

2. Description of the Background Art

Delivery of drugs by the transdermal route has been known to be theoretically possible for many years. The earliest patented transdermal devices were medicated bandages, usually with the drug mixed into the adhesive, that were designed to deliver a specific quantity of drug to a defined area of skin for a specific time. Such devices usually did not control the rate at which the drug was released. Since the 1970's interest in using the transdermal route for controlled release therapy has grown substantially.

Controlled release transdermal devices rely for their effect on the delivery of a known flux of drug to the skin for a prolonged period of time, generally a day, several days, or a week. The patch design influences and, to a certain extent, regulates the flux of drug. In one standard patch design, the drug is contained in a reservoir, with one or more layers separating the reservoir from the skin of the wearer. Typically, these layers are a synthetic membrane and an adhesive. The drug diffuses through these layers to the skin. In another common patch design, the drug is dissolved or suspended in a polymer or adhesive matrix which is in direct contact with the skin of the wearer. In this case, the drug diffuses from the matrix into the skin.

The skin is an effective barrier against the majority of drugs. Unless the delivery device is made unacceptably large, or the natural skin permeation rate of the drug is somehow increased by the use of enhancers, then the drug flux across the skin is generally inadequate for useful therapy. Thus, although in theory any drug might be delivered by this route, serious investigation of candidate drugs has been limited to those few that exhibit suitable properties, namely: small molecular size; short half-life; extensive and rapid liver metabolization, thus rendering oral administration difficult; high in vivo skin permeability; and small effective therapeutic dose, etc.

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences, e.g., gastrointestinal irritation and the like, are eliminated as well. Transdermal drug delivery also makes possible a high degree of control over blood concentrations of any particular drug.

The vast majority of transdermal systems are designed so as to deliver a drug continuously throughout the wearing period. For many drugs, however, continuous delivery poses the potential problem of tolerance. For such drugs, a continuous delivery patch must be removed periodically during the wearing period so as to prevent development of tolerance. The inconvenience of periodic patch removal can in turn create problems with patient compliance and thus with drug efficacy as well.

To date, it has been difficult to transdermally deliver tolerance-inducing drugs in therapeutically effective profiles. It is therefore desirable to provide improved devices and approaches which avoid the disadvantages of these conventional devices and methods while providing an effective means for delivering tolerance-inducing drugs.

SUMMARY OF THE INVENTION

The present invention provides a novel transdermal delivery system for the modulated administration of a drug through intact skin. In a preferred embodiment, the system is capable of delivering a drug through a patient's skin via a three-phase drug delivery profile. In the first phase or phase I, which begins with patch application and ends at about two to ten hours after patch application, plasma levels of a drug, or a metabolite, thereof are obtained. This phase is followed by a second period, or phase II, in which therapeutic plasma levels of the drug, or a metabolite thereof, are maintained. This phase begins at about two to ten hours after patch application and ends at about eight to eighteen hours after patch application. During the third period, or phase III, sub-therapeutic plasma levels of the drug, or a metabolite thereof, are maintained, via inherent patch design and/or patch removal. This delivery pattern is particularly useful for the delivery of tolerance-inducing drugs.

The transdermal delivery system comprises a backing layer; a drug reservoir; a non-rate-controlling membrane; and an adhesive layer, wherein the drug reservoir comprises a drug, a solvent-type enhancer, a plasticizer-type enhancer, and optionally a gelling agent and wherein the adhesive layer contains a plasticizer-type enhancer. In a preferred embodiment, isopropyl myristate is used as the plasticizer-type enhancer in combination with ethanol as the solvent-type enhancer. In some embodiments, the device will also comprise a release liner and a storage pouch.

A method of delivering a tolerance-inducing drug, and particularly a vasodilator, such as isosorbide dinitrate, is also described. This method comprises placing the transdermal delivery system on the skin of a patient in need of the drug and administering the drug, preferably via a three-phase modulated drug delivery pattern, through the patient's skin at a therapeutically effective dose.

DESCRIPTION OF THE PREFERRED EMBODIMENT

1. Definitions and General Parameters

Figure 1:
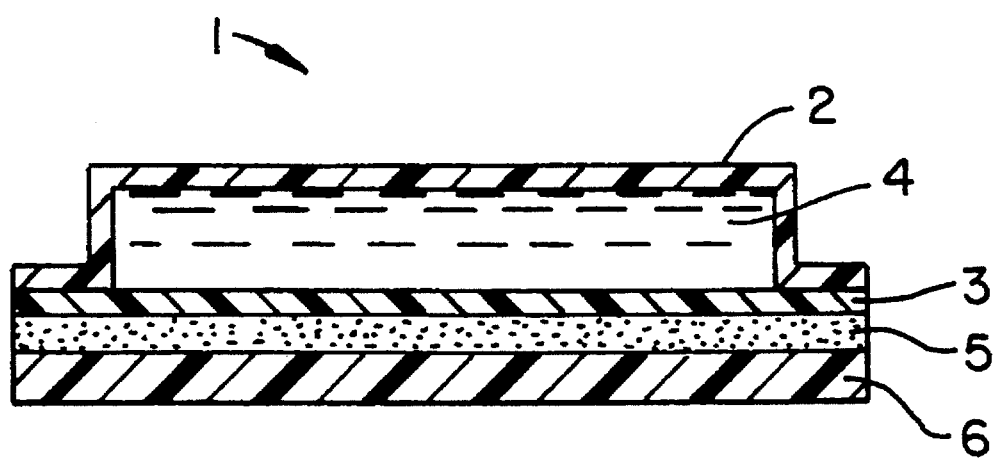
FIG. 1 is a cross-sectional view through a preferred embodiment of the transdermal delivery devices of this invention.

Unless otherwise stated, the following terms used in the specification and claims have the meanings given below:

"Drug" and "agent" are used interchangeably and are intended to have their broadest interpretation as to any therapeutically active substance which is delivered to a living organism to produce a desired, usually beneficial, effect. In general, this includes therapeutic agents in all of the major therapeutic areas.

"Lower alkyl ester of a fatty acid" refers to an ester having the formula:

$CH_3(CH_2)_d COOR$, wherein d is an integer from 6 to 22 and R is lower alkyl, for example, the lower alkyl esters of the following fatty acids: lauric, myristic, palmitic, stearic, eicosanoic, and docosanoic;

$CH_3-(CH_2)_f-(CH=CH)_g-(CH_2)_h-CO_2R$, wherein R is lower alkyl, f is an integer from 1 to 10, g is an integer from 1 to 4, h is an integer from 1 to 10, and f+g+h is an integer from 6 to 22, for example, the lower alkyl esters of the following fatty acids: palmitoleic, oleic, petroselenic, vaccenic, punicic, parinaric, gadoleic, and cetoleic; or $CH_3-(CH_2)_m-(CH=CH-CH_2)_n-(CH_2)_p-CO_2R$, wherein R is lower alkyl, m is an integer from 1 to 5, n is an integer from 2 to 5 and p is an integer from 1 to 8, and m+n+p is an integer from 6 to 22, for example, the lower alkyl esters of the following fatty acids: linoleic, linolenic; and arachidonic.

"Fatty acid" refers to a carboxylic acid having the formula:

$CH_3(CH_2)_d COOH$, wherein d is an integer from 6 to 22, for example, the following fatty acids: lauric, myristic, paimitic, stearic, eicosanoic, and docosanoic;

$CH_3-(CH_2)_f-(CH=CH)_g-(CH_2)_h-CO_2H$, wherein f is an integer from 1 to 10, g is an integer from 1 to 4, h is an integer from 1 to 10, and f+g+h is an integer from 6 to 22, for example, the following fatty acids: palmitoleic, oleic, petroselenic, vaccenic, punicic, parinaric, gadoleic, and cetoleic; or $CH_3-(CH_2)_m-(CH=CH-CH_2)_n-(CH_2)_p-CO_2H$, wherein m is an integer from 1 to 5, n is an integer from 2 to 5 and p is an integer from 1 to 8, and m+n+p is an integer from 6 to 22, for example, the following fatty acids: linoleic, linolenic; and arachidonic.

The unsaturated fatty acids and fatty acid esters occur in isomeric forms due to the presence of the one or more unsaturated positions. Either of the individual double bond isomers, as well as mixtures thereof, can be used as plasticizer-type enhancers.

"Fatty alcohol" refers to alcohols having the formula:

$CH_3(CH_2)_d CH_2OH$, wherein d is an integer from 6 to 22;

$CH_3-(CH_2)_f-(CH=CH)_g-(CH_2)_h-CH_2OH$, wherein f is an integer from 1 to 10, g is an integer from 1 to 4, h is an integer from 3 to 10, and f+g+h is an integer from 6 to 22; or $CH_3-(CH_2)_m-(CH=CH-CH_2)_n-(CH_2)_p-CH_2OH$, wherein m is an integer from 1 to 5, n is an integer from 2 to 5 and p is an integer from 1 to 8, and m+n+p is an integer from 6 to 22.

The unsaturated fatty alcohols occur in isomeric forms due to the presence of the one or more unsaturated positions. Either of the individual double bond isomers, as well as mixtures thereof, can be used as plasticizer-type enhancers.

"Polyol" refers to a compound having more than one hydroxyl group (—OH).

"Alcohol" refers to a compound having the formula R—OH or Ar—OH, wherein R is alkyl or aryl.

"Lower alkyl" refers to a cyclic, branched or straight chain alkyl group of one to six carbon atoms. This term is further exemplified by such groups as methyl, ethyl, n-propyl, i-propyl, n-butyl, t-butyl, i-butyl (or 2-methylpropyl), cyclopropylmethyl, i-amyl, n-amyl, and hexyl.

"Alkyl" refers to a cyclic, branched, or straight chain alkyl group comprising carbon and hydrogen. This term is further exemplified by groups such as methyl, heptyl, —($CH_2)_2$—, and adamantyl. Alkyl groups can either be unsubstituted or substituted with one or more substituents, e.g., halogen, lower alkyl, lower alkoxy, lower alkylthio, trifluoromethyl, lower acyloxy, and hydroxy.

"Aryl" or "Ar" refers to an aromatic carbocyclic group having a single ring (e.g., phenyl) or multiple condensed rings in which at least one ring is aromatic, (e.g., 1,2,3,4-tetrahydronaphthyl, naphthyl, anthryl, or phenanthryl), which can optionally be unsubstituted or substituted with one or more substituents, e.g., halogen, lower alkyl, lower alkoxy, lower alkylthio, trifluoromethyl, lower acyloxy, and hydroxy.

"Pharmaceutically- or therapeutically-acceptable" refers to a substance which does not interfere with the effectiveness or the biological activity of the active ingredients and which is not toxic to the host or patient.

"Pore size" or "pore" are used interchangeably and refer to holes or pathways which may be tortourous where the nominal values used to describe the pore size refer to the average of a distribution of pore sizes in the non-rate controlling membrane of the transdermal delivery system.

II. The Device

Referring now to FIG. 1, the figure shows a schematic representation of a preferred embodiment of this invention. The transdermal drug delivery device, 1, comprises an impermeable backing layer, 2, which is sealed at its periphery to a non-rate-controlling membrane, 3, thus defining a drug reservoir or depot, 4. The drug reservoir generally contains the drug, a gelling component, and permeation enhancers. An adhesive layer containing a plasticizer-type enhancer, 5, affixed to the membrane attaches the patch to the skin of a patient. Some embodiments will utilize a release liner 6. This device is designed to provide a modulated, or preferably, a three-phase drug delivery profile, i.e., an initial period in which drug or drug metabolite plasma levels are obtained, followed by a period in which therapeutic plasma levels of the drug, or a metabolite thereof, are maintained, and then a period in which sub-therapeutic plasma levels of the drug, or a metabolite thereof, are maintained.

A. The Backing Layer

The impermeable backing layer, 2, defines the top of the drug delivery device, i.e., the side furthest away from the skin when the device is in use. The backing forms an occlusive layer that prevents the loss of drug and/or enhancers to the environment and protects the patch from contamination from the environment. The backing layer is typically opaque so as to protect the drug from light.

The backing layer can be made from standard commercially available films for medical use, such as those supplied by 3M Corporation, St. Paul, Minn.; Dow Chemical, Midland, Mich.; Avery Specialty Tape Division, Painesville, Ohio.; or AF Packaging, Winston-Salem, N.C. Suitable materials which can be used to form the backing layer include films or sheets of polyolefin, polyester, polyurethane, polyvinyl alcohol, polyvinylidene, polyamide, ethylene-vinylacetate copolymer, ethylene-ethylacrylate copolymer, and the like, metal-vapor deposited films or sheets thereof, rubber sheets or films, expanded synthetic resin sheets or films, unwoven fabrics, fabrics, knitted fabrics, paper, and foils. These materials can be used individually or as laminates. These films can be pigmented or metalized.

Preferred backing layers include Scotchpak® 1006 and 1009, skin-colored aluminized polyester films of 50 μm in thickness, and 3M-1012, a transparent polyester film laminate, all of which are available from 3M Corporation.

B. The Non-Rate-Controlling Membrane

A membrane, 3, separates the drug reservoir from the adhesive layer and is generally comprised of a non-rate-controlling membrane. According to the present invention, a non-rate-controlling membrane is one in which the rate of permeation of the enhancer(s) and drug through the membrane is greater than their permeation rate through the skin (typically two to five times greater or more). Thus, a non-rate-controlling membrane is extremely permeable to the enhancer(s) and the drug contained in the reservoir.

The membrane typically is comprised of a microporous material. Microporous membranes have a distinct pore structure with pores ranging in diameter from approximately 0.01 to 3.0 microns, preferably from about 0.1 to 2.0 microns, more preferably from about 0.2 to 1.5 microns. In some embodiments, the pore size is between 0.08 and 0.5 microns. Examples of suitable microporous membranes include polyethylene and polypropylene films, nylon, and nitrocellulose film. A preferred membrane material is Cotran® 9710 and Cotran® 9711, which are polyethylene membranes, 50 μm in thickness, with a void volume of greater than 10%, available from 3M Corporation. Other embodiments of the present invention will utilize other microporous polyethylene membranes, such as Celgard K-256, available from Hoechst-Celanese, Charlotte, N.C., and microporous polyethylene films having pore sizes of from 0.1 to 5.0 microns, such as Solupor® membrane type 7P.03 and 7P2.0, available from DSM Solutech, the Netherlands.

C. The Reservoir

The membrane, 3, and the backing layer, 2, are sealed at their peripheral edges to form the drug reservoir, 4. This seal should be substantially fluid-tight so as to prevent leakage from the reservoir. As used herein, the term "peripheral edges" of the membrane and backing layers refer to the areas that are sealed together to define the drug reservoir. Therefore, extraneous membrane and backing layer material may extend outwardly from the drug reservoir and peripheral edge.

The drug reservoir contains a solution, suspension, or gel of the drug and the permeation enhancers, as well as diluents, such as water, and vehicles or other additives. The drug can be dispersed in the solution, suspension, or gel in either a dissolved or undissolved state.

i. The Drug

The only limitation to the use of this system for a drug for transdermal use is that the drug have at least one form which permeates through the skin and any barriers of the system between the drug and the skin. Examples of types of drugs that can be used in the inventive device include analgesics, anesthetics, antianginals, e.g., calcium channel blockers, antifungals, antibiotics, anticancer drugs, antiinflammatories, anthelmintics, antidotes, antiemetics, antihistamines, antihypertensives, antimalarials, antimigraine agents, antimicrobials, antipsychotics, antipyretics, antiseptics, antiarthritics, antithrombin agents, antituberculotics, antitussives, antivirals, appetite suppressants, cardioactive drugs, chemical dependency drugs, cathartics, chemotherapeutic agents, coronary, cerebral, or peripheral vasodilators, contraceptive agents, antidepressants, depressants, diagnostic aids, diuretics, expectorants, hormonal agents, hypnotics, immunosuppression agents, narcotic antagonists, parasympathomimetics, sedatives, stimulants, sympathomimetics, tranquilizers, urinary antiinfectives, vasoconstrictors, and the like. The preferred drugs are those which are effective at relatively low concentration in the blood stream.

While virtually any drug can be administered transdermally with the present system, it is especially useful to administer a tolerance-inducing drug. "Tolerance" or "therapeutic tolerance" refers to a decreased responsiveness to the pharmacologic effect of a drug from previous exposure to it or to a related drug. According to the instant invention, tolerance is also meant to include "tachyphylaxis" wherein acute tolerance occurs within minutes of drug exposure and repeated doses of a drug in a short period of time elicit sequentially smaller and smaller responses. See, e.g., U.S. Pat. No. 4,855,315 (1989); U.S. Pat. No. 4,598,094; U.S. Pat. No. 4,590,210 (1986); U.S. Pat. No. 4,476,140 (1984); U.S. Pat. No. 4,183,912; RE 30,053; U.S. Pat. No. 5,183,807; U.S. Pat. No. 5,149,786. Tolerance-inducing drugs which can be delivered using the devices described herein include, but are not limited to, those listed in Table I.

TABLE I

Tolerance-inducing Drugs

Antazoline hydrochloride
Astemizole
Azatadine maleate
Bromodiphenhydramine hydrochloride
Brompheniramine maleate
Carbinoxamine maleate
Chlorpheniramine maleate
Chlorpheniramine tannate
Clemastine fumarate
Cyproheptadine hydrochloride
Dexbrompheniramine maleate
Dexchlorpheniramine maleate
Diphenhydramine citrate
Diphenhydramine hydrochloride
Doxylamine succinate
Methdilazine hydrochloride
Promethazine hydrochloride
Terfenadine
Trimeprazine tartrate
Tripelennamine citrate
Tripelennamine hydrochloride
Metaproterenol Sulfate
Metaraminol Bitartrate
Methoxamine Hydrochloride
Phenylephrine Bitartrate;
Phenylephrine Hydrochloride
Phenylpropanolamine Hydrochloride
Atracurium Besylate
Gallamine Triethiodide
Metocurine iodide
Pancuronium bromide
Succinylcholine chloride
Tubocurarine chloride
Vecuronium bromide
Succinylcholine chloride
Nicotine polacrilex
Nicotine
Atenolol
Acebutolol hydrochloride
Captopril
Diltiazem hydrochloride
Enalapril maleate
Enalaprilat
Metoprolol tartrate
Nadolol
Nifedipine
Propranolol hydrochloride
Hydrochlorothiazide
Timolol maleate
Verapamil hydrochloride
Clonidine hydrochloride
Chlorthalidone
Guanabenz acetate
Guanethidine monosulfate
Guanadrel sulfate
Labetalol hydrochloride
Hydralazine hydrochloride
Methyldopate hydrochloride
Methyldopa and Chlorothiazide
Methyldopa and Hydrochlorothiazide
Minoxidil
Pindolol
Prazosin hydrochloride
Alseroxylon
Deserpidine
Rauwolfia Serpentina
Reserpine
Sodium nitroprusside
Trimethaphan camsylate
Amyl Nitrite
Erythrityl tetranitrate
Triprolidine hydrochloride
Amphotericin B
Imipenem
Cilastatin sodium
Primaquine phosphate
Co-trimoxazole
Sulfamethoxazole
Trimethoprim
Pentamidine Isethionate
Interferon Alfa-2a;
Interferon Alfa-2b;
Interferon Alfa-2c;
Interferon Alfa-n1;
Interferon Alfa-n3
Trihexyphenidyl Hydrochloride
Bitolterol Mesylate
Ephedrine Hydrochloride;
Ephedrine Sulfate
Isoetharine Hydrochloride;
Isoetharine Mesylate
Isoproterenol Hydrochloride;
Isoproterenol Sulfate
Mephentermine Sulfate trihydrate
Buprenorphine hydrochloride
Naltrexone hydrochloride
Fluoxetine hydrochloride
Clozapine
Amphetamine sulfate
Dextroamphetamine sulfate
Methylphenidate hydrochloride
Bendroflumethiazide
Benzthiazide
Chlorothiazide sodium
Chlorthalidone
Cyclothiazide
hydrochlorothiazide
Hydroflumethiazide
Methyclothiazide metolazone
Polythiazide
Quinethazone
Trichlormethiazide
Indapamide
Bumetanide
Ethacrynic Acid
Ethacrynate Sodium
Furosemide
Cocaine hydrochloride
Famotidine
Edetate calcium disodium
Desmopressin acetate
Lypressin
Bupivacaine hydrochloride
Chloroprocaine hydrochloride
Etidocaine hydrochloride
Lidocaine hydrochloride
Mepivacaine hydrochloride
Prilocaine hydrochloride
Procaine hydrochloride
Propoxycaine hydrochloride
Tetracaine hydrochloride
Alclometasone dipropionate
Amcinonide
Betamethasone benzoate
Betamethasone dipropionate
Betamethasone valerate
Clobetasol propionate
Clocortolone pivalate
Desonide
Desoximetasone
Dexamethasone sodium phosphate
Diflorasone diacetate
Fluocinolone acetonide
Oxitriptan

TABLE I-continued

Tolerance-inducing Drugs

Isosorbide dinitrate
Nitroglycerin
Pentaerythritol tetranitrate
Indomethacin sodium
Morphine sulfate
Hydromorphone
Oxymorphone
Methadone
Meperidine
Levorphanol
Codeine phosphate
Pentazocine
Nalbuphine
Butorphanol
Steroids
Nonsteroidal anti-inflammatory agents
Disease modifying anti-rheumatoid drugs
Salicylates
Ibuprofen
Fenoprofen
Naproxen
Piroxicam
Tolmetin
Indomethacin
Sulindac
Meclofenamate
Fentanyl
Carbidopa and Levodopa
Disulfiram
Methyldopate
HCl
Glyceryl trinitrate
Nitroglycerin absorbed on lactose
Octyl nitrite
Sodium nitrite
Clonitrate
Erythrityl tetranitrate
Mannitol hexanitrate
Pentaerythritol tetranitrate
Pentrintrol
Triethanolamine trinitrate
Trolnitrate phosphate (triethanolamine trinitrate diphosphate)
Amphetamines
Pilocarpine
Morphine
L-DOPA
Epinephrine
Nabilone
Isoproterenol
Catacholamines
Metaproterenol
Prostaglandins In a presently preferred embodiment, the tolerance-inducing drug is isosorbide dinitrate (ISDN) or metabolites thereof, such as isosorbide 2-mononitrate (IS-2-MN) or isosorbide 5-mononitrate (IS-5-MN). Isosorbide dinitrate is a vasodilator which can be used to relieve the pain associated with angina pectoris, for the prevention of angina, in hypertension, for relaxation of involuntary muscles of blood vessels mainly arteries and arterioles, for increasing the flow of blood therein, and for increasing oxygenation from vasodilation, mainly for increasing the supply of oxygen to the heart.

The amount of drug in the reservoir ranges from about 0.1 to about 70% by weight (wt %), based on the reservoir fill solution, and preferably from about 0.5 to about 40 wt %. In the embodiment wherein isosorbide dinitrate is delivered with the device of the present invention, the amount of drug will range from about 0.1 to about 10 wt %, and more preferably from about 0.5% to about 5 wt %. In the exemplary device described below, ISDN is present in the reservoir at about 2 wt %.

ii. The Enhancers

The device of the present invention employs a combination of permeation enhancers in the reservoir layer typically comprising a plasticizer-type enhancer and a solvent-type enhancer. In addition, a plasticizer-type enhancer is employed in the adhesive layer.

"Plasticizer-type enhancer" refers to fatty acids and fatty alcohols that are capable of increasing the permeability of drugs to the stratum corneum. Without limiting the scope of the present invention, the following is proposed as the mechanism of action of plasticizer-type enhancers. It is believed that the function of these plasticizer-type enhancers is to migrate into the upper stratum corneum layers of the skin and to remain there for a prolonged period of time. The stratum corneum layer, although only 25–50 microns thick, is the principal barrier to transdermal permeation. The plasticizer-type enhancers that migrate into the skin serve to increase the mobility and solubility of the drug into the skin.

Plasticizer-type enhancers generally will have a molecular weight of greater than 150 but less than 1000. In addition, the plasticizer-type enhancer should also be relatively water insoluble or it will leach into the subcutaneous tissue layers below the stratum corneum. Thus, plasticizer-type enhancers with water solubility of less than 0.5 wt % are preferred, and more preferably 0.2 wt % or less.

Enhancers may also be classified according to their Hildebrand solubility parameters. The Hildebrand solubility parameter measures the cohesive forces and sum of all intermolecular attractive forces related to the extent of mutual solubility of many chemical species. See, e.g., Barton (1975) Chem. Rev. 75:731; Vaughan (1985) J. Soc. Cosmet. Chem. 36:319; and CRC Handbook of Solubility Parameters and other Cohesion Parameters, CRC Press, Inc.: Boca Raton, Fla. (1985). Relative hydrophilicity increases with the value of the Hildebrand solubility parameter ($\delta$). For example, the skin has a $\delta$ value of 10, while water has a $\delta$ value of 23.4. This implies that enhancers with solubility parameters <10 will intervene with the lipid component of the skin, but those with solubility parameters >10 will selectively partition into the polar components in skin. Generally, plasticizer-type enhancers are considered to have a $\delta$ value of between about 5 and 10. A particularly preferred plasticizer-type enhancer, isopropyl myristate, has a $\delta$ value of about 8.

A preferred group of plasticizer-type enhancers includes lower alkyl esters of pharmaceutically-acceptable fatty acids, fatty acids, fatty alcohols, and similar hydrophobic compounds. Examples of fatty acid esters include isopropyl myristate, isopropyl palmitate, and the methyl and ethyl esters of oleic and lauric acid. In addition, fatty alcohols, such as stearyl alcohol and oleyl alcohol, can be used as plasticizer-type enhancers. Fatty acids that can be used as plasticizer-type enhancers include oleic acid, lauric acid, myristic acid, palmitic acid, stearic acid, linoleic acid, and palmitoleic acid. In addition, many other compounds can also serve as plasticizer-type enhancers, such as diethyl hexyl phthalate, octyldodecyl myristate, isostearyl isostearate, caprylic/capric triglyceride, glyceryl oleate, hexamethyldisiloxane, dimethicone, cyclomethicone, squalene, mineral oil, macrocyclic ketones/lactones, and various oils, such as wintergreen or eucalyptol.

One of skill in the art will appreciate that the plasticizer-type enhancers may be used alone or in combination. A particularly preferred plasticizer-type enhancer is isopropyl myristate.

"Solvent-type enhancer" generally refers to relatively hydrophilic compounds having molecular weights less than about 200 that are capable of increasing the permeability of drugs to the stratum corneum. Solvent-type enhancers typically exhibit solubility parameters between about 10 and 24, and preferably between about 10 and 18. Solvent-type enhancers are often better enhancers because they generally provide higher flux rates than plasticizer-type enhancers. Typically, the solvent-type enhancer will comprise a pharmaceutically-acceptable lower alkyl alcohol, an aryl alcohol, or a polyol, for example, ethanol, propanol, butanol, benzyl alcohol, glycerin, and propylene glycol.

Other embodiments will employ an alkyl ether, such as ethylene glycol ether, polyethylene glycol ether, and propylene glycol ether, as the solvent-type enhancer. Preferred examples of ethylene glycol ethers include, but are not limited to, ethylene glycol monoalkyl ethers, such as ethylene glycol monomethyl ether (also known as methyl Cellosolve), ethylene glycol dialkyl ethers, such as ethylene glycol dimethyl ether (also known as dimethyl Cellosolve), and ethylene glycol monoalkyl ether esters, such as ethylene glycol monoethyl ether acetate (also known as Cellosolve acetate). Preferred examples of polyethylene glycol ethers include, but are not limited to, diethylene glycol monoalkyl ethers, such as diethylene glycol monobutyl ether (also known as butyl ethyl Cellosolve or butyl Carbitol), diethylene glycol dialkyl ethers; and diethylene glycol monoalkyl ether esters, such as diethylene glycol monoethyl ether acetate (also known as Carbitol acetate).

Preferred solvent-type enhancers have a molecular weight of less than about 150. They are also relatively hydrophilic, generally being greater than 2 wt % soluble in water, and are preferably greater than 10 wt % soluble in water. Most preferred solvent-type enhancers are completely water miscible. One of skill in the art will appreciate that the solvent-type enhancers may be used alone or in combination. Preferred solvent-type enhancers include lower alkyl alcohols, with a most preferred solvent-type enhancer being ethanol.

While these solvent-type enhancers can be useful in delivering therapeutic agents through the skin when used alone, large amounts of the enhancer often must be applied continuously to get a prolonged therapeutic effect. As such, they are often irritating to the skin. However, when a plasticizer-type enhancer is used in combination with a solvent-type enhancer, drugs can be delivered through the stratum corneum at therapeutically effective levels. Such a synergistic enhancer mixture achieves high delivery rates of the drug with lower concentrations of the solvent-type enhancer. This eliminates the irritation that occurs when solvent-type enhancers are used alone at high concentrations without plasticizer-type enhancers.

When used with plasticizer-type enhancers, the function of the solvent-type enhancer is to rapidly diffuse into the stratum corneum layer of the skin making it possible for the heavier, less mobile plasticizer-type enhancer to enter the stratum corneum layer. The small size and hydrophilic nature of these solvent-type enhancers makes them very effective in this role.

In general, the total amount of plasticizer-type enhancer will be less than the solvent-type enhancer. For example, a ratio of about 1 part plasticizer-type enhancer to at least about 10 parts solvent-type enhancer is preferred, with about 1 part to about 20 or greater parts, being more preferred. Typically, the solvent-type enhancer is present in the reservoir in an amount from about 10 to about 80 wt %, based on the reservoir fill solution, preferably, in a range from about 20 to about 75 wt %, and more preferably, in a range from about 50 to about 70 wt %. Hence, the solvent-type enhancer is typically present in amount between 250 and 1500 mg, preferably between about 250 and 1000 mg and more preferably, between about 500 and 1000 mg. Typically, the plasticizer-type enhancer is present in the reservoir in an amount from about 0.1 to about 30 wt %, based on the reservoir fill solution, preferably, in a range from about 0.5 to about 15 wt %, and more preferably, in a range from about 1 to about 5 wt %.

iii. The Gelling Agent

A gelling agent optionally is incorporated into the reservoir to increase the viscosity and rheological characteristics of the drug and enhancers. The agent also serves to prevent settling of the dispersed drug during storage. Typically, a viscosity range of about 100 to 10,000 centipoise for the combination of materials forming the reservoir is necessary in order to produce the drug delivery device using form-filling technology, as described in greater detail below.

A detailed description of techniques for the determination of viscosity measurements can be found in GELVA®, Multipolymer Resins for Pressure Sensitive Adhesives, Publication No. 8092. Briefly, viscosity is measured at 25.0°±0.5° C. using a Brookfield viscometer with speed ranges of 6, 12, 30, or 60 rpm and spindles #1, 2, 3, or 4. The sample to be tested should be free of trapped air.

The gelling agent comprises a pharmaceutically-acceptable material that is capable of increasing viscosity of the reservoir solution. Typically, the drug delivery devices described herein will employ cellulosic materials as the gelling agent. Examples of suitable cellulosic materials include cellulose, cellulose derivatives, alkylcellulose, hydroxy-(lower alkyl)cellulose derivatives where the alkyl group contains one to six carbons, carboxyalkylcellulose and the like. Other gelling agents include PVP, CMC, Klucel, alginates, kaolinate, bentonite, or montmorillonite, other clay fillers, stearates, silicon dioxide particles, carboxy polymethylene, ethylene maleic anhydride, polyacrylamide, and poly (methyl vinyl ether maleic anhydride).

A preferred embodiment of the present invention utilizes a hydroxy-(lower alkyl)cellulose as the gelling agent. Typically, hydroxypropylcellulose will be employed in an amount from about 0.1 to about 20 wt %, based on the reservoir fill solution, and preferably from about 0.5 to about 10 wt %. In the example described below, the gelling agent is present in about 2 wt %.

iv. Additional Components

The reservoir layer also may include diluents, stabilizers, vehicles, biocides, antioxidants, anti-irritants and the like. For example, water is frequently utilized as a diluent in the reservoir. Typically water will be present in the reservoir in an amount not greater than about 50 wt %, based on the reservoir fill solution; preferably, not greater than 40 wt %; and more preferably, not greater than about 30 wt %. Other diluents which will-frequently find use in the drug delivery devices described herein include glycerine and propylene glycol.

In addition, drugs are frequently available as stabilized solutions or solid triturates. For example, ISDN can be purchased as a solution in the following vehicles: ethanol, mineral oil, benzyl alcohol, polyethylene glycol, and propylene glycol. ISDN may-also be purchased as a stabilized solid triturate, in combination with lactose, mannitol, sorbitol, or other sugars. Thus, when the drug is incorporated into the reservoir layer, the reservoir will also contain the vehicle or solvent used to produce the initial drug solution.

v. A Preferred Embodiment

The reservoir for a preferred drug delivery device, described in detail below, comprises from about 0.5 to about 10 wt % of a drug, from about 10 to about 75 wt % of a $C_2$–$C_4$ alcohol as the solvent-type enhancer, from about 0.5 to about 15 wt % of a plasticizer-type enhancer, and from about 0.1 to about 10 wt % of the gelling agent, with the balance being water. A preferred combination for a reservoir device comprises about 0.5 to about 10 wt % of a drug, from about 30 to about 70 wt % of ethanol as the solvent-type enhancer, from about 1 to about 5 wt % of isopropyl myristate, and from about 0.1 to about 10 wt % of hydroxypropylcellulose as the gelling agent, with the balance being water.

D. The Adhesive Layer

A pressure-sensitive adhesive layer, 5, is affixed to the membrane opposite to the backing layer. A pressure sensitive adhesive is generally a material which adheres to a surface with slight pressure and releases from the surface with negligible transfer of the adhesive to the surface. Ideally, the adhesive layer should not permit excessive migration of the fill solution from the reservoir into the adhesive during storage; it should not interact with the drug; it should adhere firmly to the membrane, but removably to the peel strip; it should stick securely to the wearer for extended periods, yet allow the transdermal delivery device to be removed with minimum discomfort; and it should not give rise to skin irritation, allergic reactions or other dermatological problems. These properties must be maintained from the time of patch manufacture, throughout storage, and up to and throughout the time of application.

Generally, the selection of the adhesive is important to the proper functioning of the transdermal delivery device. This is particularly true when a plasticizer-type enhancer is placed in the adhesive layer, as in the present invention. Specifically, the adhesive layer must retain its functioning properties in the presence of the plasticizer-type and solvent-type enhancers, as well as upon exposure to the drug of choice. However, often enhancers or other formulation ingredients can compromise the physicochemical and functional properties of an adhesive. Significant loss of cohesive strength can result in undesirable effects such as an increase in tack, cold flow beyond the edge of the patch, transfer of adhesive to the protective release liner during removal, or adhesive residue left on the skin following removal of the patch. In some cases, the patch loses adhesion altogether and falls off. The loss of tack and other adhesion properties generally dictates and limits the amount and type of enhancers that can be loaded into the adhesive matrix type patches. In addition, as the structural integrity of the dosage unit is lost, the delivery rate of the drug is diminished and/or becomes variable and unstable.

For example, silicone adhesives are commonly used in transdermal delivery devices; however, they are capable of a maximum compatible loading of only about 1% isopropyl myristate. See Pfister et al. (1990) *Pharm. Tech. Int.* 55–59, Pfister and Hsieh (1991) *Pharm. Tech. Int.* 3:28–32, and Pfister and Hsieh (1991) *Pharm. Tech. Int.* 3:32–36. Since the adhesive layer of the devices described herein contain a high level of plasticizer-type enhancer, typically from about 5 to about 50 wt % of a plasticizer-type enhancer, based on the adhesive layer, and preferably from about 10 to about 40 wt %, and more preferably from about 25 to about 35 wt %, the proper selection of the adhesive is crucial to the performance of these transdermal delivery devices.

Preferably, the adhesives employed in the transdermal delivery systems described herein will have shear values greater than 2 min, with higher values being preferred; plasticity values between about 1 mm and 4 mm and preferably greater than 1.5 mm, with the higher values being preferred; tack values between about 50 grams and 1000 grams, with values of less than 500 grams being preferred; a dynamic loss modulus between about $10^3$ and $10^6$ Pa measured at a frequency of $10^{-2}$ and about $10^4$ and $10^6$ Pa measured at a frequency of $10^2$ rad/sec, respectively; with the intermediate values being preferred; and a dynamic storage modulus between about $10^3$ and $10^6$ Pa measured at a frequency of $10^{-2}$ rad/sec and about $10^4$ and $10^6$ Pa measured at a frequency of $10^2$ rad/sec, respectively, with the intermediate values being preferred (see Chang, (1991) *J. Adhesion* 34:189–200 and European Patent Publication No. 524,776. Cross-linked acrylate-based adhesives, such as those available from Avery Chemical Division, Mill Hall, Pa. and National Starch and Chemical Company, Bridgewater, N.J., are able to withstand relatively high loading of enhancers, both solvent-type and plasticizer-type, while still maintaining these performance parameters. These adhesives generally contain about 1 to about 5 wt % of acrylic acid, about 5 to about 20 wt % of a $C_4$ to a $C_{12}$ alkyl acrylate or alkyl methacrylate. The adhesives also can contain about 0.1 to about 5 wt % of a cross-linking monomer.

Preferred acrylate-based adhesives include Avery 2533 adhesive (available from Avery Chemical Division (U.S.), Mill Hall, Pa.), AS-460HPX (available from Avery Chemical Division (U.S.), Mill Hall, Pa.), Duro-tak® 9852 (available from National Starch, Bridgewater, N.J.), and Monsanto's Gelva GE 1753. A preferred embodiment of the present invention employs GE 1753 or AS-460HPX. More preferably, Duro-tak® 9852 is used as the adhesive.

Typically the adhesive forms a continuous layer across the entire surface of the device; however, in some embodiments of the instant invention, the adhesive is disposed as a ring surrounding the active area of the patch.

E. The Release Liner

Optionally, the invention may include a peel strip or release liner. This covers the surface of the pressure-sensitive adhesive during storage, and prevents evaporative loss of the drug or enhancer(s) that may have migrated into the adhesive layer. The release liner may be formed with dimples for decreasing contacting surface with the adhesive layer, and it may also be formed with a pull-tab for making it easier for removing it from the device.

The peel strip may be made from any impermeable film, such as is specified for the backing layer. Additionally it may be made from metal foil, Mylar® polyethylene terephthalate, or any material normally used for this purpose in the art that is compatible with the drug and the chosen adhesive. Examples of suitable compositions for the release liner include siliconized polyester, poly(1,1-dihydroperfluoroctylmethacrylate), fumed silica in silicone rubber, end-capped siliconized polyethylene terephthalate, polytetrafluoroethylene, cellophane, treated paper, siliconized paper, siliconized kraft paper, aluminized paper, paper coated with polyethylene, a film of polyvinyl chloride having titanium dioxide dispersed therein, and the like. A preferred release liner comprises a fluoropolymer coated polyester film, such as 3M Scotchpak® 1022 film. The 3M Scotchpak® film 1022, as described above, is a preferred choice.

F. Storage Pouches

Prior to use, the patches typically are stored in foil pouches, both to prevent contamination and to avoid drug and/or enhancer(s) loss. The pouch should be alcohol resistant. Such pouches are standard in the industry. A typical pouch comprises a laminate of various materials, for example, those shown below in Table II.

TABLE II

| General Description | Source | Composition (outer layer to inner layer) |
|---|---|---|
| Storage Pouches | | |
| Polyethylene | Lithotype Co., San Francisco, CA | 5 g/m² paper, 12 μm LDPE[1], 9 μm Al[2], 38 μm LDPE |
| Surlyn | Lithotype Co. | 57 g/m² paper, 12 μm LDPE, 8 μm Al, 78 μm Surlyn |
| Polypropylene metalized film | James River Corp., San Leandro, CA | 19 μm OPP[3], 17 μm LDPE, Al, 15 μm OPP, 5 μm PP[4] |
| 305W | Ivers-Lee, a division of Becton-Dickinson, West Caldwell, NJ | 194HB23 Cello, 19 μm WLDPE[5], 13 μm Al, 4 μm 3% EA[6] copolymer |
| 406 | Ivers-Lee | 30 lb paper, 18 μm LDPE, 13 μm Al, 25 μm Surlyn |

TABLE II-continued

| General Description | Source | Composition (outer layer to inner layer) |
|---|---|---|
| Storage Pouches | | |
| Acrylonitrile butadiene copolymer film laminate | Jefferson Smurfet, Alton, IL. | 48 gauge polyester film, 18 μm ethylene copolymer, 9 μm Al, adhesive L-4020, 50 μm Barex® 210 Film[7] |
| Ethylene acrylic acid copolymer | James River Corp. | 14 μm OPP, 17 μm LDPE, 8 μm Al, 23 μm LDPE, 15 μm EA |

[1] LDPE = low-density polyethylene
[2] Al = aluminum foil
[3] OPP = orientated polypropylene
[4] PP = polypropylene
[5] WLDPE = white low density polyethylene
[6] EA = ethylene acrylic acid copolymer
[7] Barex® 210 Film is an acrylonitrile butadiene copolymer available from BP Chemicals International.

III. Assembly

The patch may be assembled by any of the techniques known in the art for laminating transdermal patches, however, typically, form-fill-seal technology is employed. A mixture of the adhesive and the plasticizer-type enhancer is cast onto the release liner. The membrane material is affixed to the adhesive. The membrane is then peripherally heat-sealed to the backing. The drug is incorporated into the reservoir by, first, preparing a solution of drug, enhancers, water, and gelling agent. The drug formulation is then dispersed onto either the backing or membrane.

Figure 8:
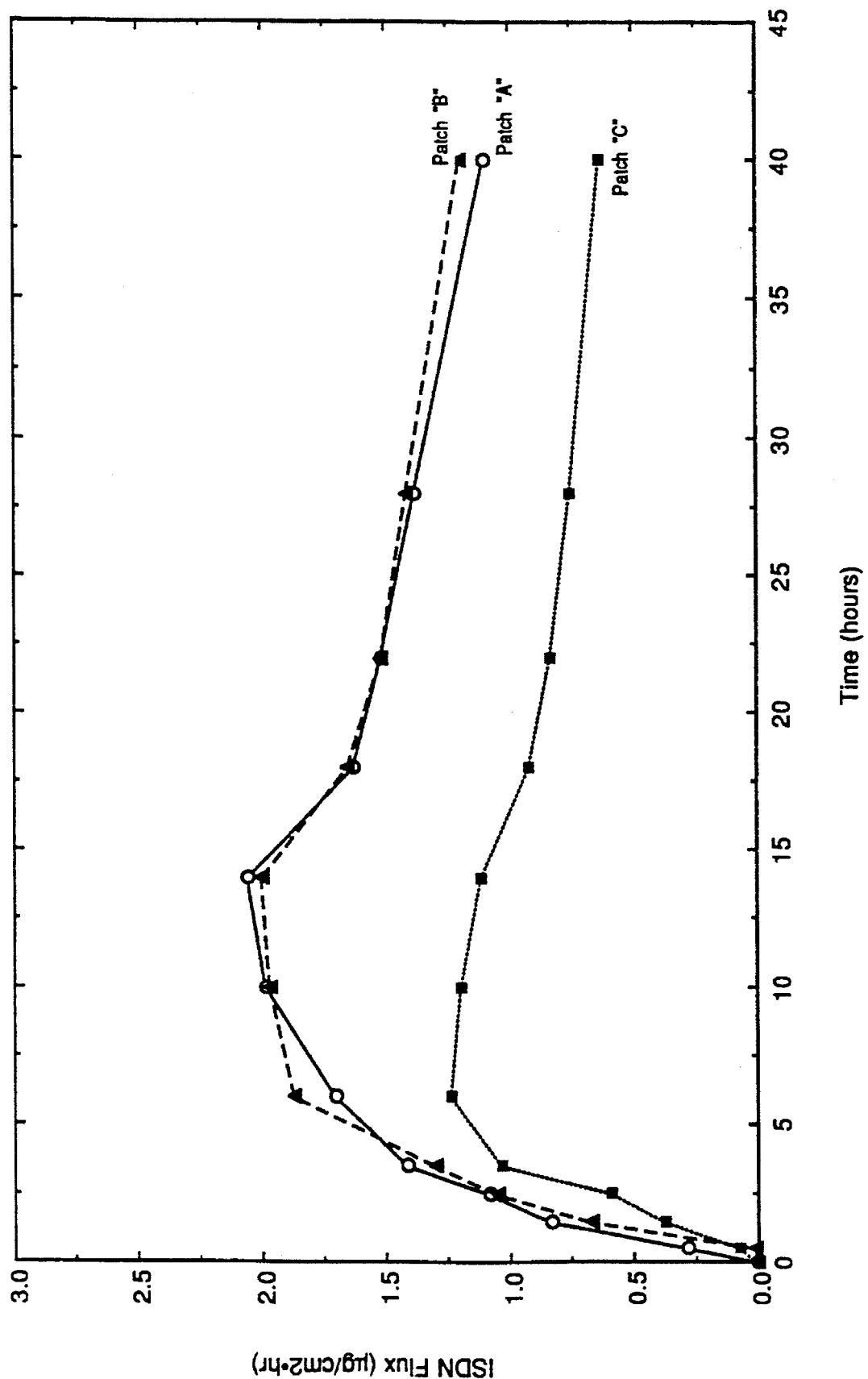
FIG. 8 is a comparative plot of in vitro drug flux (micrograms ($\mu$g) per square centimeter ($cm^2$) per hour (hr)) through porcine skin as a function of time (hours) for embodiments of this invention having variations in the reservoir fill solution composition on drug flux.
Figure 9:
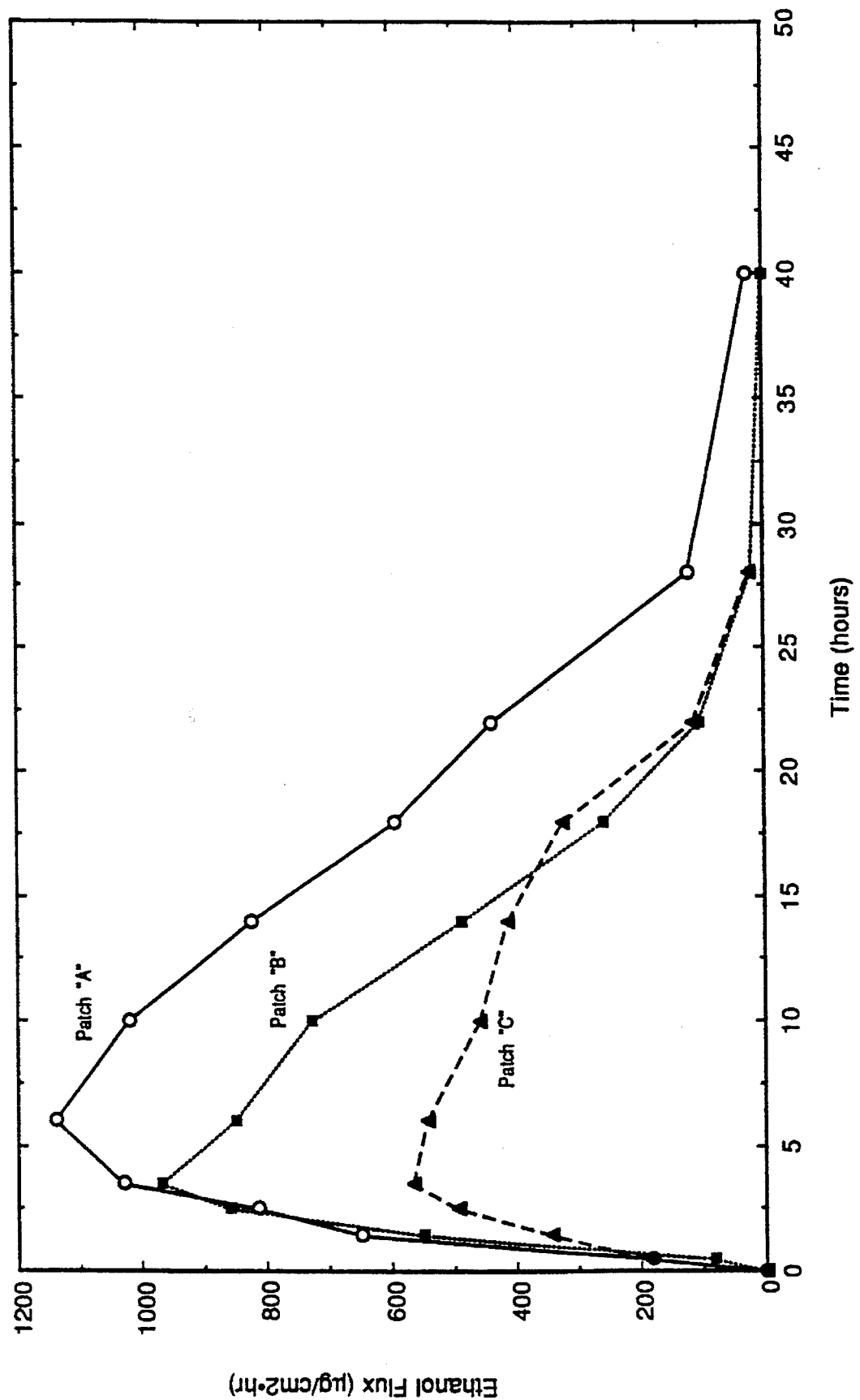
FIG. 9 is a comparative plot of in vitro ethanol flux (micrograms ($\mu$g) per square centimeter ($cm^2$) per hour (hr)) through porcine skin as a function of time (hours) for embodiments of this invention having variations in the reservoir fill solution composition on drug flux.

Both the total volume of the reservoir fill solution (and therefore the absolute quantities of drug and enhancer(s) and the percentage by weight of drug and enhancer(s) in the reservoir can be widely varied while still effecting the desired three-phase delivery profile. As discussed above, the drug content of the finished patch can vary from about 0.1 to about 70 wt %. More specifically, the quantity of drug contained in the reservoir will typically range from about 5 to about 50 mg. The effect of variations in reservoir fill solution composition on drug flux is shown in FIGS. 8 and 9.

The drug delivery device useful for the present purpose can have various shapes, such as oblong, square, round, rectangular, and the like. The round form is particularly preferred as it contains no corners which might be easily detached from the skin.

In addition to having various shapes, the dosage units produced may come in various sizes. A total surface area in the range of 1 to 200 cm² is contemplated and the presently preferred sizes are 5–100 cm², with 5–30 cm² being more preferred. The active surface area will typically be somewhat less than the total surface area and generally is in the range of 1 to 190 cm², with 5–95 cm² being preferred, and 5–25 cm² being more preferred.

The thickness of the drug delivery device of the present invention may vary over a wide range but is preferably 2.5 to 5 millimeters (mm) and particularly preferably 3.5 to 4 mm thick. The weight of the drug delivery device will typically be less than 5 grams, and preferably less than 3 grams. The fill volume of the reservoir typically will be between about 200 mg and 1.5 g, preferably between about 200 mg and 1.2 g. Typically, the total amount of plasticizer-type enhancer in the reservoir and the adhesive will be between about 25 and 200 mg, preferably between about 50 and 150 mg, and more preferably, between about 50 and 100 mg.

IV. Drug Delivery Profile

Figure 2:
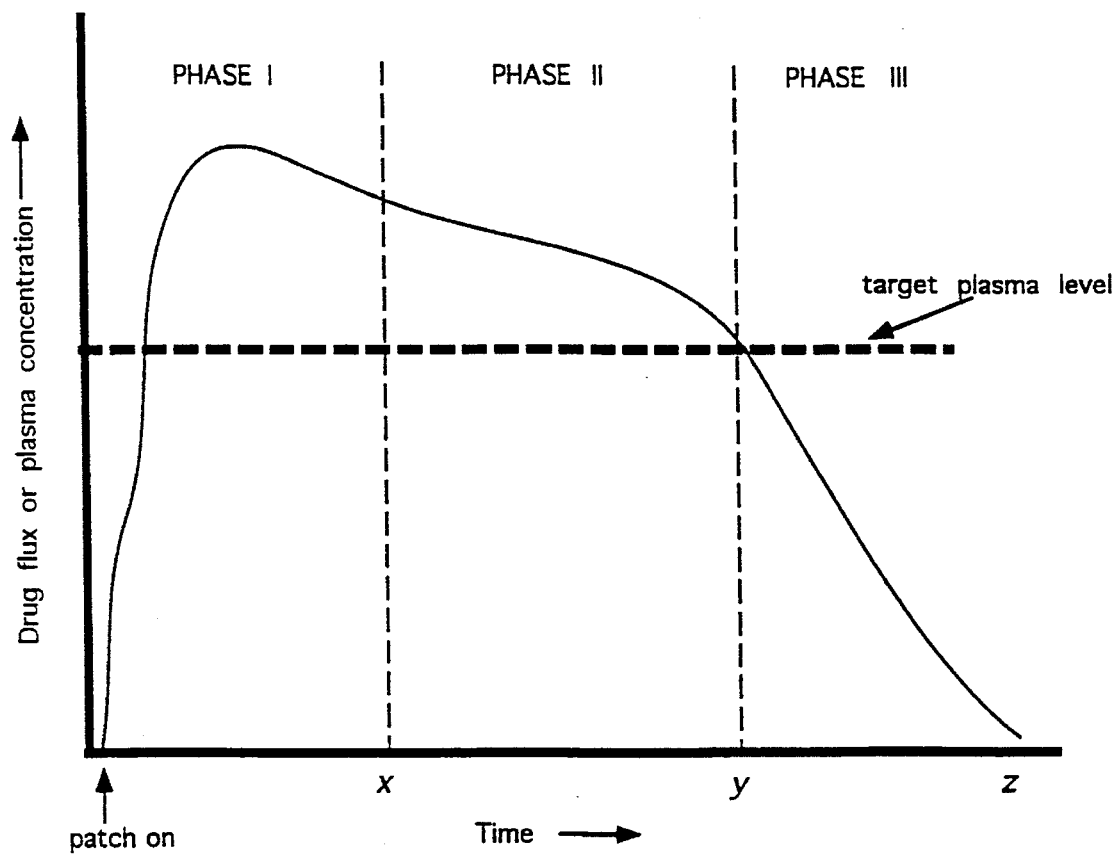
FIG. 2 is a plot of the modulated drug delivery profile resulting from the administration of tolerance-inducing drugs using the transdermal delivery system described herein.

The present system enables a modulated, and preferably a three-phase drug delivery pattern over an approximately 24-hour drug delivery period. This modulated drug delivery pattern can be characterized by an initial period in which drug or drug metabolite plasma levels are obtained. This period begins with patch application and ends at about two to ten hours after patch application. Typically during this period, the maximal drug delivery rate occurs (see Phase I of FIG. 2).

During the second phase of the modulated drug delivery pattern, therapeutic plasma levels of the drug, or a metabolite thereof, are maintained. This phase typically begins at two to ten hours after patch application and ends at about eight to eighteen hours after patch application (see Phase II of FIG. 2). According to some embodiments, the drug may possess more than one therapeutic plasma level, depending on the indication. Thus, the second phase of the modulated drug delivery pattern may encompass the delivery of drugs at more than one therapeutic plasma level.

A final period then occurs in which sub-therapeutic levels of the drug, or a metabolite thereof, are obtained. This period may be inherent in the patch design or result from patch removal.

Figure 3:
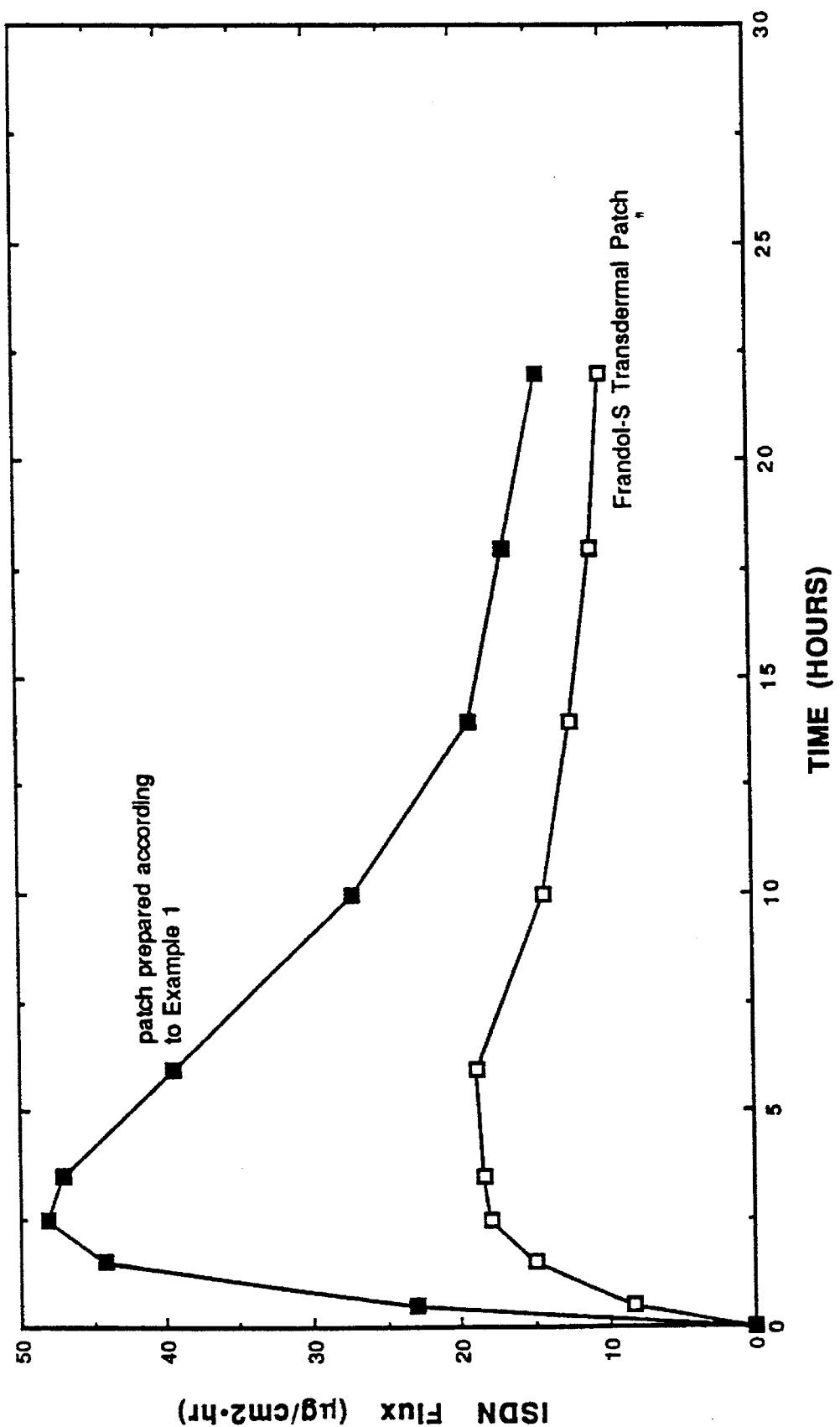
FIG. 3 is a plot of in vitro drug flux (micrograms (µg)/square centimeter ($cm^2$).hour (hr)) through skin as a function of time (hours) for an embodiment of this invention described in greater detail (solid squares), as well as a comparative example (open squares) for the Frandol® Tape-S ISDN patch. The data for the comparative example was taken from the package insert provided with the commercially available Frandol® Tape-S ISDN patch.
Figure 4:
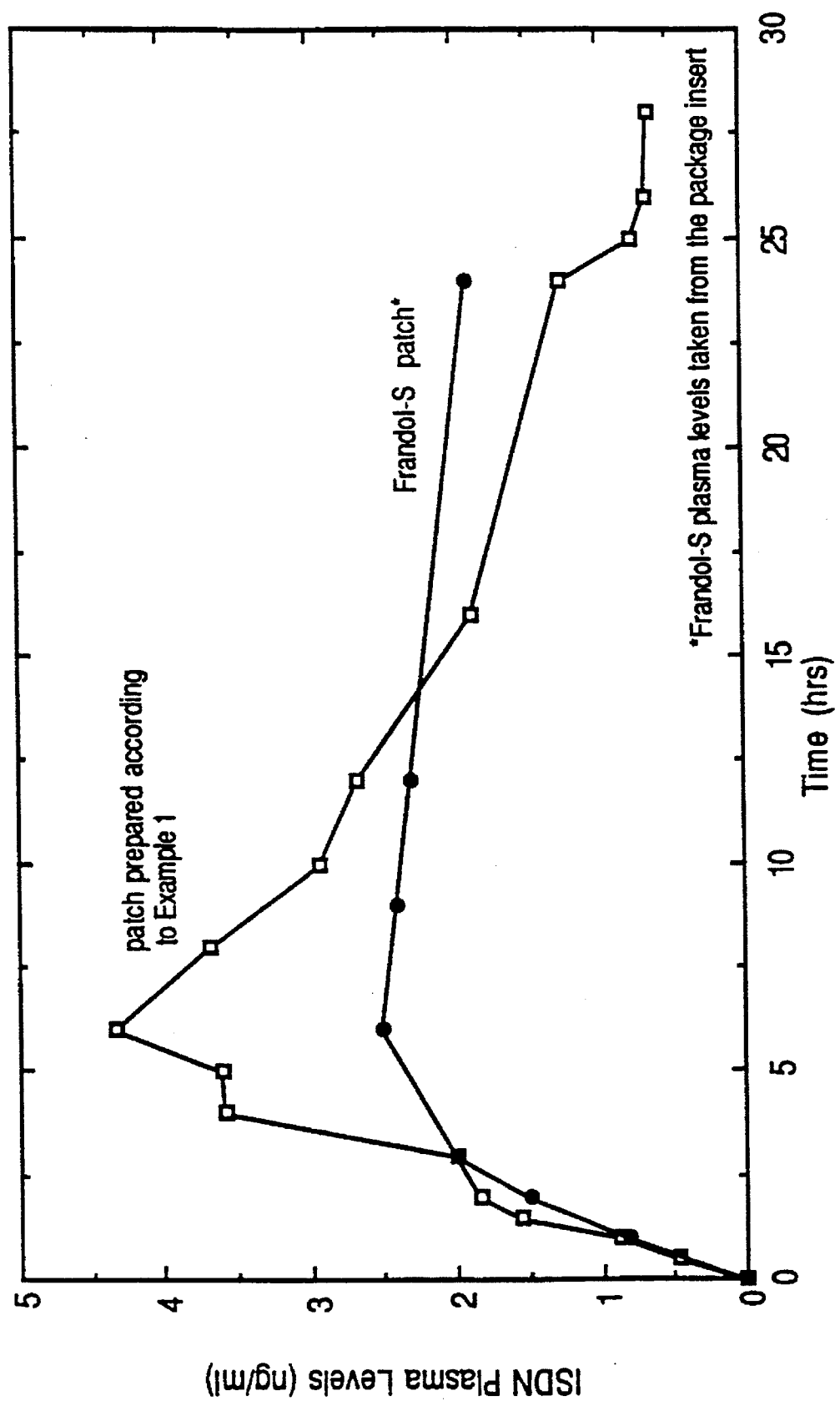
FIG. 4 is a plot of ISDN plasma levels (nanograms (ng)/milliliter (ml)) as a function of time (hours) for an embodiment of this invention described in greater detail below (squares), as well as a comparative example for the Frandol® Tape-S ISDN patch (circles). The data for the comparative example was taken from the package insert provided with the commercially available Frandol® Tape-S ISDN patch.

FIG. 3 shows a plot of the in vitro drug flux through the skin as a function of time for the embodiment of this invention described in greater detail below, as well as the flux for a comparative example, the Frandol® Tape-S ISDN patch. FIG. 4 shows a plot of the in vivo blood plasma levels of ISDN as a function of time for the embodiment of this invention described in greater detail below, as well as the blood plasma levels resulting from a comparative example, the Frandol® Tape-S ISDN patch. These figures illustrate that the devices described herein provide both a higher level of drug delivery (e.g., 50 µg/cm² hr in vitro for the device described in FIG. 3 as compared to 18 µg/cm² hr in vitro for the comparative example) and more importantly, a higher degree of modulation in the drug delivery profile than the comparative example. In addition, as shown by FIG. 4, the device described herein delivered approximately five-fold more ISDN in a 16-hour period than the comparative example.

The rationale behind this drug delivery profile is that the initial high blood levels may be more effective when followed by a period of decreasing dosage than if the blood levels were maintained either at the higher or lower level throughout the entire administration period. This modulated delivery profile is essential to effective nitrate therapy where tolerance can be avoided by an interval, typically in the range of about 6 to 10 hours, in which sub-therapeutic plasma levels of the nitrate drug, or a metabolite thereof, are obtained. Thus, the device described herein is capable, by virtue of its modulated drug delivery profile, of preventing or greatly reducing the onset of tolerance to the drug being administered.

The development of tolerance during therapy with some drugs, in particular with nitrates, such as ISDN, is a relevant therapeutic problem. Tolerance can be circumvented by dose regimens in which sub-therapeutic plasma levels of the drug, or a metabolite thereof, are maintained. Particularly in the case of ISDN, this sub-therapeutic interval is needed because two vasoactive metabolites, IS-2-MN and IS-5-MN accumulate in the plasma during continuous therapy. IS-5-MN is the major metabolic product of ISDN, has the slowest rate of elimination, and is thought to be responsible for the long duration of action of ISDN and for the development of tolerance.

Figure 10:
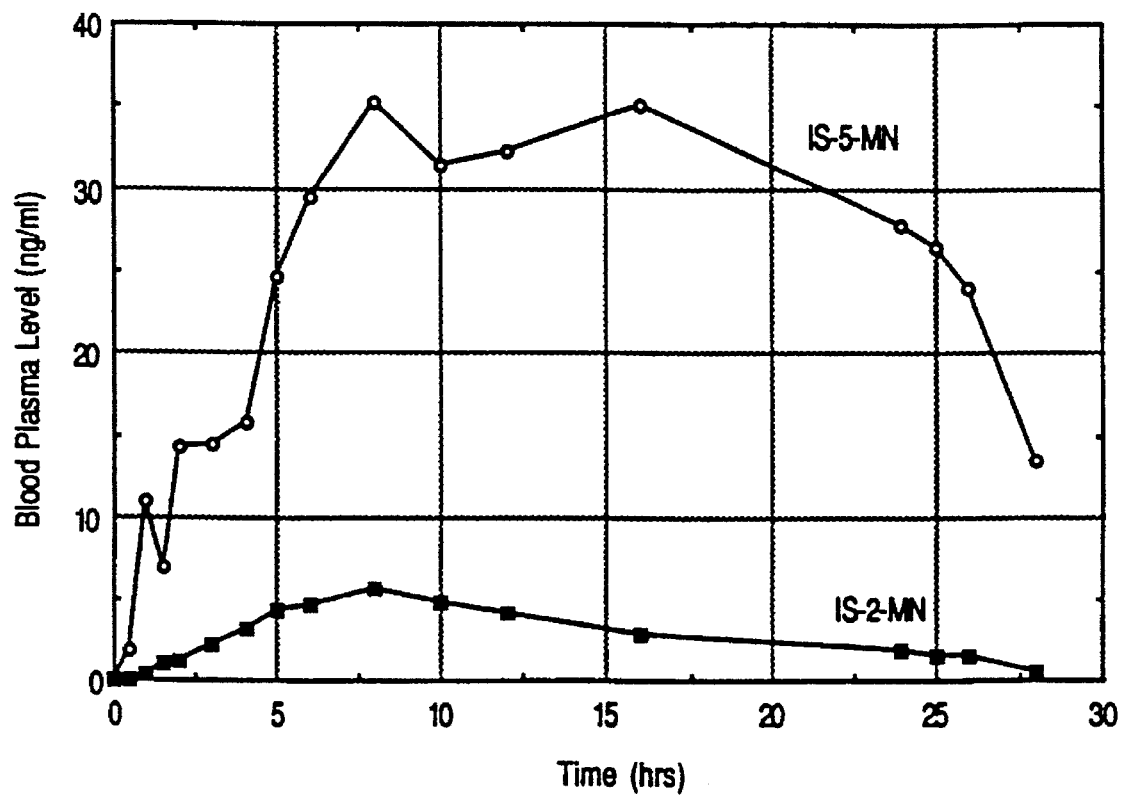
FIG. 10 is a plot of IS-2-MN and IS-5-MN plasma levels (nanograms (ng) per milliliter (ml)) as a function of time (hours) for an embodiment of this invention described in Example 1.

Several studies have shown that dose regimens of ISDN and IS-5-MN that allow the plasma concentrations of IS-5-MN to fall below 100 nanograms (ng)/milliliter (ml) before administration of the next dose have continuous antianginal efficacy. When the IS-5-MN plasma levels drop intermittently to below 100 ng/ml, the responsiveness of the vascular system is maintained. Development of tolerance is not observed. See Boertz and Bonn (1986) *Z. Kardiol.* 75 [Suppl. 3]:57; Wagner et al. (1990) *Eur. J. Clin. Pham. Suppl.* 1:s53; and Silber et al. (1985) Abstracts of the 58th Scientific Sessions, *Circulation* 72:III-431, p. 1267. As shown in FIG. 10, with the transdermal delivery system described herein employing ISDN as the tolerance-inducing drug, IS-5-MN plasma levels were maintained at less than 40 ng/ml. Thus, these devices are effective as a means of delivering tolerance-inducing drugs while reducing the risk of tolerance.

Without limiting the scope of the present invention, the following is proposed that the drug delivery profile of the device described herein results from the combination of a non-rate-controlling membrane, a combination of plasticizer-type and solvent-type enhancers in the drug reservoir, and an additional amount of plasticizer-type enhancer in the adhesive layer. While the delivery profile provided herein is primarily determined by the aforementioned factors, typically certain additional factors should be optimized, for example, the amount of fill solution; the degree of drug loading; and the diffusivity of the drug through the skin. For example, with respect to drug loading and delivery, the duration of the delivery phase is determined by the total amount of drug in the system which is in turn determined by the reservoir thickness and drug concentration in the reservoir; and the delivery rate, which is a function of the drug to be delivered, the composition of the drug delivery device, and the skin permeability of the drug.

Typically, the drug delivery device described herein will produce an initial in vivo drug delivery rate of from about 0.5 to about 40 ng/ml, preferably from about 0.5 to about 30 ng/ml, more preferably from about 0.5 to about 20 ng/ml for a period of from about 2 to about 8 hours. This initial drug delivery period will be followed by a period of gradually decreasing drug delivery. Generally, the drug delivery rate will fall below a therapeutic plasma level at about 8 to 18 hours, at which point, according to some embodiments, the patch is removed. Typically, the period of gradually decreasing drug delivery will display first-order kinetics, i.e., the drug delivery rate is dependent on the concentration of the drug being delivered.

The drug delivery devices described herein can be utilized to deliver drugs for either prophylactic and/or therapeutic treatments. In therapeutic applications, the drug is administered to a patient already suffering from a disease in an amount sufficient to cure or at least partially arrest the symptoms of the disease and its complications. An amount adequate to accomplish this is defined as the "therapeutically effective amount or dose" or the "therapeutic plasma level". An amount below the therapeutically effective amount or dose or therapeutic plasma level is termed the "sub-therapeutically effective amount or dose" or the "sub-therapeutic plasma level". Amounts effective for this use will depend on the severity and course of the disease, previous therapy, the patient's health status and response to the drugs, and the judgment of the treating physician. See, e.g., American Medical Association (1992) *Drug Evaluations Subscriptions*; and *Physicians' Desk Reference*, 46th Ed. For example, in the case of angina pectoris, a therapeutically effective amount or dose of a vasodilator, such as isosorbide dinitrate, is an amount sufficient to relieve the pain associated with angina pectoris, to relax the involuntary muscles of blood vessels and to increase the flow of blood therein, or to increase oxygenation from vasodilation, thus increasing the supply of oxygen to the heart.

In prophylactic applications, the drug delivery device described herein is employed to deliver drugs to a patient susceptible to or otherwise at risk of a particular disease. Such an amount is defined to be a "prophylactically effective amount or dose." In this use, the precise amounts again depend on the patient's state of health, weight, and the like.

Typically, the drug delivery device is applied such that a daily dose in an amount from about 0.1 to about 40 milligrams (mg), and preferably from about 0.5 to about 20 mg, of drug is delivered. In the embodiment described in detail hereinbelow, the drug isosorbide dinitrate is preferably in an amount from about 5 to about 20 mg, and preferably from about 5 to about 10 mg. The dosage may, however, also be higher or less and will be determined by the physician in each case.

A specific example of the composition of this invention is set forth below.

In order that the invention described herein can be more fully understood, the following examples are set forth. It should be understood that these examples are for illustrative purposes only, and are not to be construed as limiting this invention in any manner.

EXPERIMENTAL

EXAMPLE 1

Preparation of ISDN Reservoir Drug Delivery Device

1. Production of adhesive casting solution

An adhesive mixture of 17.2 wt % isopropyl myristate in Avery Dennison AS 2533 acrylic solvent-based adhesive (equivalent to 30 wt % of isopropyl myristate in the dry adhesive film) was prepared. The solution was allowed to degas by sitting undisturbed prior to casting.

2. Production of membrane-adhesive-release liner laminate

The coating process was carried out using conventional knife-over-roll technology. The adhesive casting solution was placed into a pressure vessel and pressured to 30 pounds per square inch (psi) using dry nitrogen. The adhesive casting solution was then fed into a coating trough having a width of 21.6 centimeters (cm). At the beginning of the coating process, the height of the blade on the coating knife was set at 230 microns (μm). Once uniformity of coating was achieved (typically within 7 minutes), the exact basis weight of the coating was adjusted to give a coating weight of 7.7 milligrams (mg)/square centimeter ($cm^2$) by using a gamma back scatter thickness gauge. The coating was applied onto the fluoropolymer coated side of a clear polyester release liner (Scotchpak® 1022, 3M Company) at a line speed of 1 foot (ft)/minute. The oven temperature was set at 55° C. and the radiant heater was set at 85% of full power. The adhesive side of the coated release liner was laminated to a microporous polyethylene membrane (Cotran® 9710, 3M Company) and rolled. The membrane-adhesive-release liner laminate was slit on a precision slitter to yield rolls 450 feet long of webs 3 inches in width.

3. Production of ISDN fill solution

A fill solution of ISDN (USP, 2.0 wt %), anhydrous ethanol (USP, 65.8 wt %), water (3.25 wt %), and isopropyl myristate (2.0 wt %) was prepared. The fill solution was mixed until homogeneous using an air driven propeller blade. Hydroxypropylcellulose (NF, 2.0 wt %) was added stepwise and mixed until dissolved. The mixture was allowed to stand at 40° C. to prevent recrystallization of the ISDN and was then de-gassed under slight vacuum.

4. Patch production

The fill solution was poured into a pressure can for feeding to a precision dispensing system on the form-fill-seal (FFS) machine. The solution was pressurized to 20 psi using helium (USP). Following adjustment of the fill weight to 1.1 grams and alignment of the web stocks, dispensing point, sealing die, and die punch, patch production was initiated. The FFS machine produced a small indentation in the 3-inch width backing film to prevent lateral flow of the dispensed fill solution. The fill solution (1.10 grams) was placed into the indentation as the web was advanced. In a continuous process, the membrane-adhesive-release liner laminate was placed on top of the filled backing web and then the backing web was advanced to the heat seal station where the webs were sealed at a die temperature of 190° C. The sealed web advanced to the die cutting station and was cut-punched into circular patches having a surface area of 25.6 $cm^2$. The production rate was approximately 20 to 25 patches/minute with a total of 1,000 patches being produced in a lot.

5. Pouching/labeling

Pouches were produced on a packaging machine from an acrylonitrile butadiene copolymer film laminate consisting of an outer white pigmented polyester aluminized on the inner side and coated with the heat seal Barex polymer layer (LCFLEX 81703, Jefferson Smurfet Corporation). The pouches (74 millimeters (mm)×76 mm) were imprinted with the lot number and production code number.

EXAMPLE 2

Adhesion Test Methods

1. General

General methods for evaluating the properties of adhesive films are described below. The following testing methods were followed for all samples. Additional testing procedures can be found in Blance (1970) U.S. Pat. No. 3,532,708, which is expressly incorporated herein by reference. The testing results for several adhesives are given below in Table IV.

2. Shear Strength

The tensile shear strength of the adhesive layer is measured by determining the maximum tension required to break the bond between the test surface and the adhesive surface of a transdermal patch or the adhesive surface of a raw material laminate. The time for the adhesive bond of the test specimen to separate from the test surface is measured by applying a constant shear stress in the same plane as the adhesive surface. The shear value is directly related to the cohesive strength of the adhesive, rather than its adhesive strength as measured by tack and peel. A low shear value indicates that the adhesive has poor cohesive strength and may leave residue on the skin when the patch is removed. A high shear value indicates that the adhesive has good cohesive strength. The static shear test involves laminating a 0.5 inch wide test specimen which is several inches in length to a smooth stainless steel test panel using a 4.5 lb rubber roller such that a length of 0.5 in of test strip overlaps the test panel resulting in a bond area of 0.25 sq. in. The specimen is allowed to equilibrate at room temperature (25° C.) for 30 minutes. Then a 500 g test weight is suspended from the end of the test strip which is held in a vertical position. The time in minutes required for the test strip to separate and fall off the test panel is recorded as the static shear value. Shear strengths of less than 2.0 min were considered unacceptable, with the higher values being preferred.

3. Tack Tests

The tack of pressure sensitive adhesive films is determined using an inverted digital probe technique. The instrument controls the contact pressure, the dwell time, and the rate of separation of the probe from the surface of the adhesive. This method meets the required equipment and application standards established by ASTM D14. See, e.g., Test Methods for Pressure Sensitive Tapes, 9th Ed., Developed by the Specifications and Technical Committee of the Pressure Sensitive Tape Council, Deerfield, Ill. The results are reported in grams and reflect the tack of the adhesive under specific operating conditions.

4. Measurement of the peel force at 180° and/or 90° angles

The peel adhesion is measured by determining the force per unit width required to break the bond between the transdermal patch adhesive and a steel plate. The transdermal patch sample is peeled back at 180° or 90° from the steel plate at a standard rate of 12 inches/minute, under ambient conditions. The testing procedure involves the use of an Instron tensile tester equipped with a 20-lb load cell and data acquisition/analysis software. Adhesive failure wherein the adhesive peeled cleanly from the steel plate was considered acceptable whereas cohesive failure wherein a residue of the adhesive was left on the steel plate was regarded as unacceptable.

A solution of adhesive composition was coated on a sheet of 2 mil gauge Scotchpak® 1022 in such a manner as to produce a uniform, dry layer of adhesive of about 30 g/M². This adhesive sheet was laminated to a sheet of 2 mil gauge untreated polyester by overlaying one edge upon the polyester sheet, adhesive side down and rolling a rubber-covered steel roller; 3.25 inches diameter by 1.75 inches wide weighing approximately 4.5 pounds (available from U.S. Testing Co., Hoboken, N.Y.) in a manner to avoid inclusion of air pockets. Strips of about 10-inch length and 1-inch width were cut from the laminate sheet. Beginning at one end of the strip, the laminate was carefully pulled apart for a distance of about 1 inch. These ends were placed in the jaws of a tensile machine so that they were straight and as taut as possible. The tensile machine was operated so that the jaws traveled at 40 inches/minute and the release force was read at least five times at equally spaced intervals between 2 inches and 8 inches, averaged, and recorded as the 900 release strength.

For the 180° adhesion test, about one inch was peeled back from a 1-inch wide strip of laminate prepared as described above. The laminate was slowly peeled apart for a distance of 6 to 6½ inches and lowered adhesive side down directly onto a clean stainless steel panel in such a manner that one end touched first and the rest of the length followed smoothly to avoid trapping air bubbles and forming wrinkles. The rubber-covered steel roller was immediately drawn over the strip, without application of any additional pressure, lengthwise, without stopping, once from each direction, at a rate of about 2 inches/second. The laminate was allowed to stand undisturbed for 20±5 minutes. The tab end was freed from the panel and gripped in the upper jaw of a tensile machine and the panel gripped in the lower jaw so that the strip was peeled off the panel at 180 degrees. The tensile machine was operated so that the jaws traveled at 12 inches/minutes. After 1 inch of the strip had been peeled off, the force was recorded and read at least five times at equally spaced intervals between 2 and 8 inches, averaged, and recorded as the 180° release strength. Detailed procedures can be obtained from Dow Corning Corporation, Midland, Mich., as CTM 0964A.

5. Plasticity testing

Plasticity is a measure of the resistance to flow of an adhesive at elevated temperature under a constant compressive load for a defined length of time.

A solution of the adhesive composition was cast using a 12.0 mil gap casting blade to form two films of coatweight of approximately 6.0 ml. The films were dried at ambient temperature for 10 minutes and then at 74.0°±1.0° C. for one hour in a circulating air oven. The films were removed from the oven and cooled to ambient conditions for 15 minutes. With a fresh razor blade, the adhesive films were scored into approximately ½ inch squares. Sufficient pressure was applied to score the adhesive, but not to cut the paper. The adhesive film was rolled into pellets approximately ⅛ inch in diameter. The small pellets were grasped between the thumb and forefinger and additional adhesive was picked up by bringing the pellet down on fresh adhesive film at right angles to the plane of casting and then picking straight up. This "up and down" adhesive pickup motion is termed "daubing".

Periodically the pellet was rotated while daubing to insure a relatively spherical shape to the final pellet. The daubing and shaping procedure was continued until a pellet weight of 2.00±0.01 grams was formed.

Two pieces of release liner, approximately 2.5"×2.5" were cut. The liner was placed between the compression plates of a Williams Plastometer, Model P-4, or equivalent plastometer, and the thickness of the liners were measured to ±0.01" on the plastometer gauge. The liners were removed from the plastometer plates and the pellet was placed between the glazed sides of the liners. The liner/pellet construction was placed in the plastometer oven at 38° C. for 20 minutes. The liner/pellet construction was then placed between the compression plates of the plastometer and the load weight was lowered to begin compression. At the end of 14 minutes, the thickness of the pellet and papers was recorded to ±0.01" on the plastometer gauge. The Williams plasticity was calculated by subtracting the thickness of the papers from the final 14.0 minute reading on the plastometer gauge.

TABLE IV

Evaluation of Adhesives

| Adhesive[8] | Peel (lb/in)[9] 0% IPM | Peel (lb/in)[9] 30% IPM | Plasticity (mm)[10] 0% IPM | Plasticity (mm)[10] 30% IPM | Tack (gm)[11] 0% IPM | Tack (gm)[11] 30% IPM | Static Shear (min)[12] 30% IPM |
|---|---|---|---|---|---|---|---|
| AS 2533[13] | 3.9[14] | 1.04[14] | 2.68 | 1.82 | 909 | 210 | 6 |
| AS 460 HPX[16] | 3.38[14] | 0.79[15] | 2.85 | 1.94 | 612 | 260 | 7 |
| GE 1753[16] | 3.14[14] | 1.10[14] | 3.09 | 1.62 | 727 | 242 | 124 |
| 80-1074[17] | 2.56[14] | 0.6[14] | 3.03 | 1.92 | 450 | 243 | 17 |
| Aroset 1930-TH-45[18] | 4.55[14] | 1.46[14] | 2.60 | 1.87 | 964 | 273 | 8 |
| Aroset 1820-Z-52[18] | 2.65[14] | 0.82[14] | 2.85 | 1.86 | 751 | 238 | 2 |
| Aroset 1860-Z-45[18] | 3.42[14] | 1.07[14] | 3.12 | 1.73 | 853 | 225 | 9 |
| DT 9852[17] | 3.10[14] | 1.40[14] | 3.44 | 2.07 | 568 | 260 | 379 |

[8]Casting conditions: 30 minutes at room temperature, 5 minutes at 100° C.
[9]Crosshead Speed: 12 minutes/minutes. Dwell time: 10 minutes.
[10]Dwell time: 14 minutes.
[11]Probe speed: 1 cm/second. Contact time: 1 second.
[12]500 grams weight. Dwell time: 30 minutes.
[13]Available from Avery.
[14]Adhesive failure.
[15]Cohesive failure.
[16]Available from Monsanto.
[17]Available from National Starch
[18]Available from Ashland

EXAMPLE 3

Preparation and testing of ISDN transdermal patches

ISDN transdermal patches were prepared in accordance with the procedures set forth in Example 1. DOW Saranex 2025 was used as the backing and Celgard K256 constituted the microporous membrane. The adhesive layer was prepared from Avery 2533 with 30% (based on adhesive solids weight) isopropyl myristate.

Figure 5:
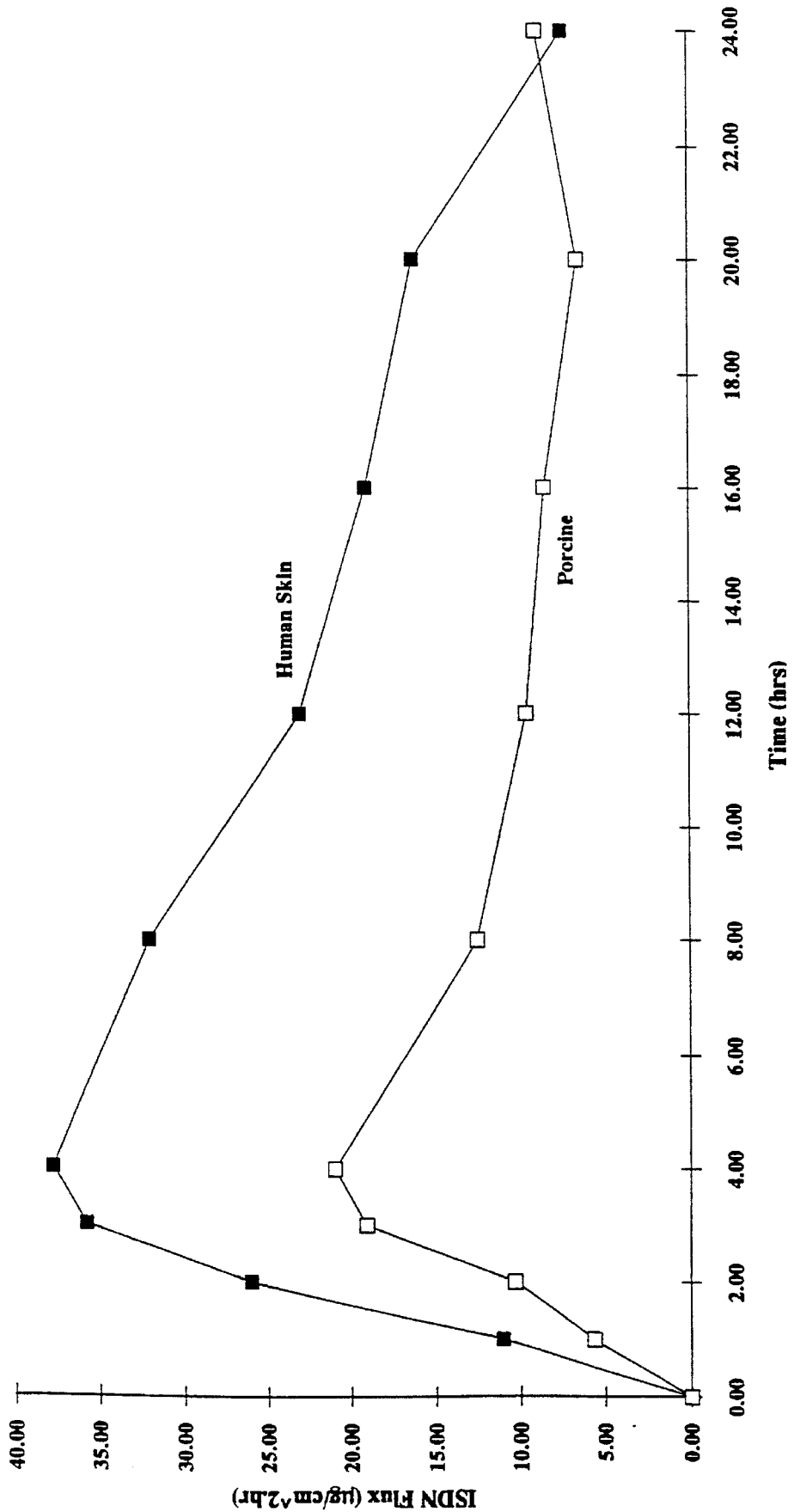
FIG. 5 is a comparative plot of in vitro drug flux (micrograms ($\mu$g) per square centimeter ($cm^2$) per hour (hr)) through human and porcine skin as a function of time (hours) for an embodiment of this invention described in detail in Example 3 below.

The in vitro skin permeation rate of ISDN was measured using flow-through diffusion cells with an active area of 1 cm$^2$ and a receiving volume of 3 ml. The receptor fluid, isotonic saline, was pumped into and through the cells, by a peristaltic pump. Samples were collected in glass vials arranged in an automatic fraction collector. Human or porcine skin was placed on the lower half of the diffusion cell with the stratum corneum facing the donor compartment. The transdermal device was placed on the stratum corneum and the amount of drug permeated across the skin (μg/cm$^2$) was calculated from the cumulative release. The resulting human and porcine skin permeation rates are shown in FIG. 5.

EXAMPLE 4

Figure 6:
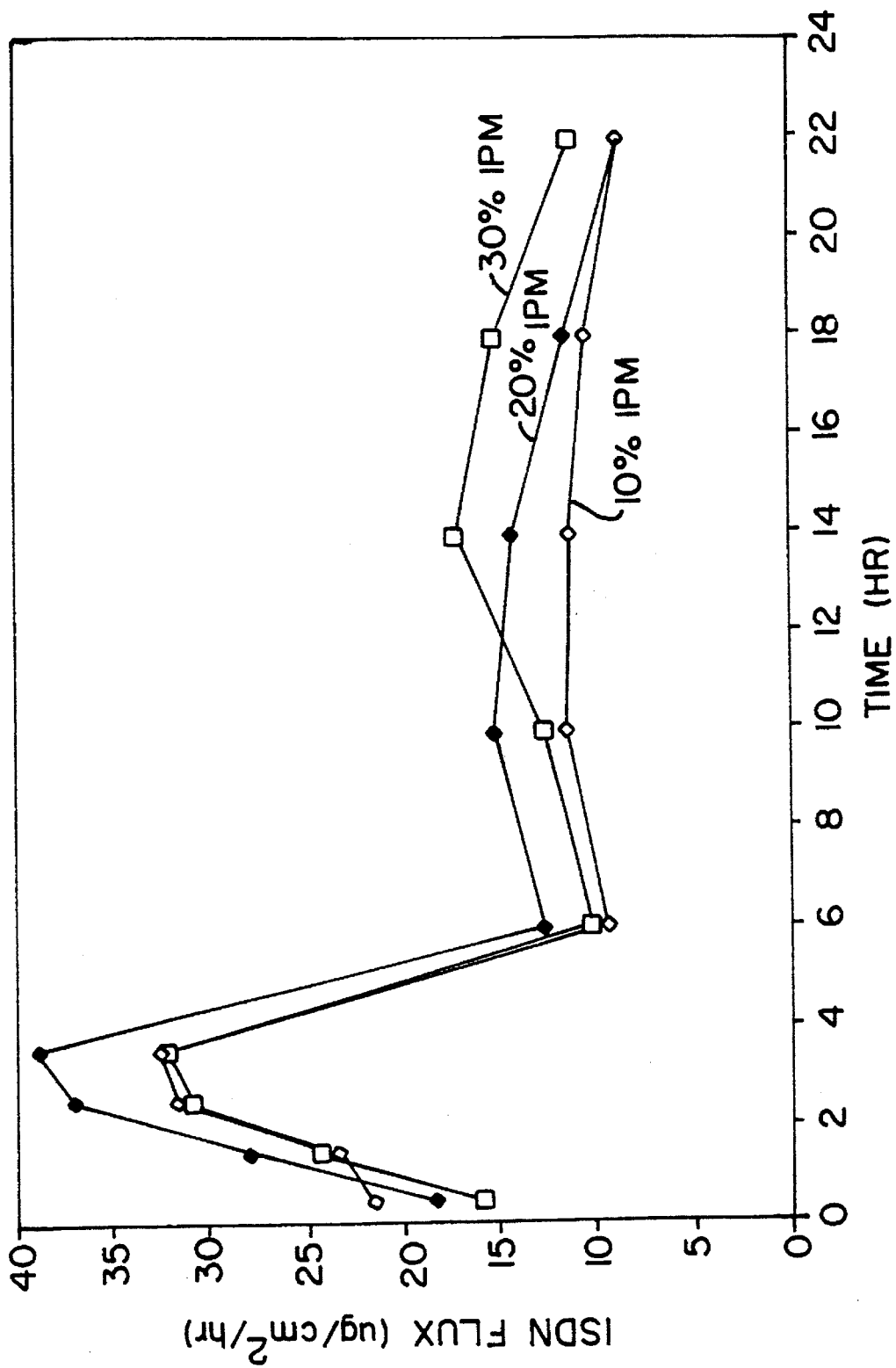
FIG. 6 is a comparative plot of in vitro drug flux (micrograms ($\mu$g) per square centimeter ($cm^2$) per hour (hr)) through porcine skin as a function of time (hours) for an embodiment of this invention described in detail in Examples 3 and 4 below with differing levels of plasticizer-type enhancer in the adhesive layer.

Preparation and testing of ISDN transdermal patches with different amounts of enhancer in the adhesive ISDN transdermal patches with differing amounts of isopropyl myristate (10%, 20%, or 30%) in the adhesive (Avery 2533) were prepared according to the procedure of Example 1. The ISDN in vitro skin permeation rate of ISDN through porcine skin was measured according to the procedure in Example 3 and is shown in FIG. 6.

EXAMPLE 5

Figure 7:
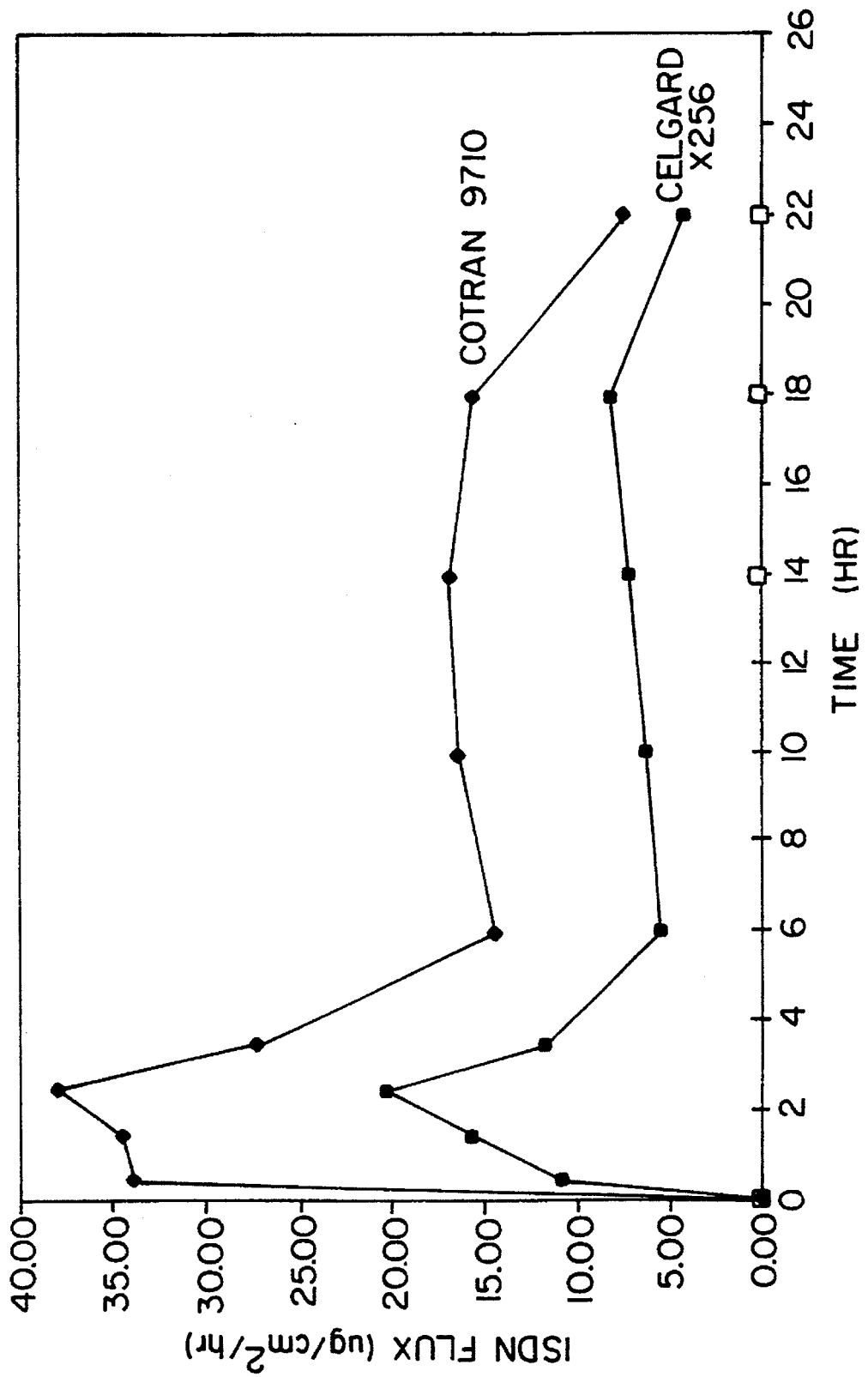
FIG. 7 is a comparative plot of in vitro drug flux (micrograms ($\mu$g) per square centimeter ($cm^2$) per hour (hr)) through porcine skin as a function of time (hours) for an embodiment of this invention described in detail in Examples 3 and 5 below employing two different microporous membranes.

Preparation and testing of ISDN transdermal patches with different microporous membranes ISDN transdermal patches were prepared according to the procedures set forth in Example 1 using either Cotran 9710 or Celgard K256 as the microporous membrane. The ISDN in vitro skin permeation rates of ISDN through porcine skin were measured for each of these patch types according to the procedure of Example 1 and are shown in FIG. 7.

EXAMPLE 6

Preparation and testing of ISDN transdermal patches with different fill compositions and different drug reservoir loading ISDN transdermal patches were prepared according to the procedures of Example 1. The composition of the drug reservoir fill solution was varied as shown in Table III below:

TABLE III

Reservoir Compositions for ISDN Patches

| | Patch "A" | Patch "B" | Patch "C" |
|---|---|---|---|
| Wt % Ethanol | 67.0 | 67.0 | 67.6 |
| Wt % Water | 28.7 | 28.7 | 28.9 |
| Wt % ISDN | 2.4 | 2.4 | 28.9 |
| Wt % Hydroxypropyl-cellulose | 1.9 | 1.9 | 1.9 |
| Mg of fill solution | 300 | 200 | 300 |
| Mg Ethanol | 201 | 134 | 203 |
| Mg ISDN | 7.2 | 4.8 | 4.2 |

All other patch components (i.e, backing, membrane, adhesive with isopropyl myristate) were as specified in Example 1. The ISDN in vitro skin permeation rates of ISDN and of ethanol through porcine skin were measured for Patches A, B, and C, according to the procedures in Example 3 and are shown in FIGS. 8 and 9.

The disclosures in this application of all articles and references, including patent documents, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A transdermal delivery patch for the administration of a drug through intact skin, said patch comprising:
   (a) a backing layer;
   (b) a membrane adjacent to said backing layer, wherein said membrane is in contact with said backing layer to form a peripheral substantially fluid-tight seal and to define a reservoir therebetween;
   (c) a drug, a solvent-type enhancer, and a plasticizer-type enhancer in said reservoir;
   (d) said membrane having a pore size diameter between about 0.01 and about 3.0 microns and being non-rate controlling to said drug and enhancers in said reservoir; and
   (e) an adhesive layer over said membrane on the outside of said reservoir for contact with skin and through which drug and enhancers permeate, said adhesive layer containing about 10–40% by weight of a plasticizer-type enhancer and being selected to retain its functioning properties therewith,
   wherein a modulated three-phase drug administration pattern is obtained when said patch is contacted with skin, said pattern having:
   (i) a first period in which plasma levels of said drug or a metabolite thereof are obtained, wherein said first period begins at patch application and ends at about two to ten hours after patch application;
   (ii) a second period in which therapeutic plasma levels of said drug or a metabolite thereof are maintained, wherein said second period begins at about two to ten hours after patch application and ends at about eight to eighteen hours after patch application; and
   (iii) a third period in which sub-therapeutic plasma levels of said drug of a metabolite thereof are maintained, wherein said third period begins at about eight to eighteen hours after patch application.

2. The device of claim 1, wherein said membrane has a pore size of between about 0.08 and 0.5 microns.

3. The device of claim 1, wherein said drug comprises a tolerance-inducing drug.

4. The device of claim 3, wherein said tolerance-inducing drug is selected from the group consisting of isosorbide dinitrate, isosorbide 2-mononitrate and isosorbide 5-mononitrate.

5. The device of claim 4, wherein said tolerance-inducing drug comprises isosorbide dinitrate.

6. The device of claim 1, wherein said drug is present in said reservoir in an amount of from about 0.1 to about 70% by weight of the reservoir contents.

7. The device of claim 6, wherein said drug is present in said reservoir in an amount of from about 0.5 to about 40% by weight.

8. The device of claim 1, wherein said plasticizer-type enhancer in said reservoir is selected from the group consisting of lower alkyl esters of fatty acids, fatty acids, and fatty alcohols.

9. The device of claim 8, wherein said plasticizer-type enhancer in said reservoir comprises a lower alkyl ester of a fatty acid.

10. The device of claim 9, wherein said plasticizer-type enhancer in said reservoir comprises isopropyl myristate.

11. The device of claim 1, wherein said solvent-type enhancer is selected from the group consisting of lower alkyl alcohols, aryl alcohols, and polyols.

12. The device of claim 11, wherein said solvent-type enhancer comprises a lower alkyl alcohol.

13. The device of claim 12, wherein said solvent-type enhancer comprises ethanol.

14. The device of claim 1, wherein the ratio of said plasticizer-type enhancer to said solvent-type enhancer in said reservoir is from about 1 part of plasticizer-type enhancer to at least about 10 parts of solvent-type enhancer.

15. The device of claim 14, wherein the ratio of said plasticizer-type enhancer to said solvent-type enhancer in said reservoir is from about 1 part of plasticizer-type enhancer to at least about 20 parts of solvent-type enhancer.

16. The device of claim 1, wherein said reservoir further comprises a gelling agent.

17. The device of claim 16, wherein said gelling agent comprises hydroxypropylcellulose.

18. The device of claim 16, wherein said gelling agent is present in said reservoir in an amount from about 1 to about 20% by weight.

19. The device of claim 18, wherein said gelling agent is present in said reservoir in an amount from about 1 to about 10% by weight.

20. The device of claim 1, wherein said plasticizer-type enhancer in said adhesive layer is selected from the group consisting of lower alkyl esters of fatty acids, fatty acids, and fatty alcohols.

21. The device of claim 20, wherein said plasticizer-type enhancer in said adhesive layer comprises isopropyl myristate.

22. The device of claim 1, wherein said plasticizer-type enhancer in said adhesive layer is present in an amount from about 25 to about 35% by weight.

23. The device of claim 1, wherein said adhesive layer comprises a cross-linked acrylate-based adhesive.

24. The device of claim 1, further comprising a release liner.

25. The device of claim 1, further comprising a storage pouch.

26. A method for administering a drug to a patient in need of such administration, said method comprising:
   (a) applying on the skin of said patient a transdermal delivery system for the modulated administration of a drug through intact skin comprising:
   (1) a backing layer;
   (2) a membrane adjacent to said backing layer, wherein said membrane is in contact with said backing layer to form a peripheral substantially fluid-tight seal and to define a reservoir therebetween;
   (3) a drug, a solvent-type enhancer, and a plasticizer-type enhancer in said reservoir;
   (4) said membrane having a pore size diameter between about 0.01 and 3.0 microns and being non-rate controlling to said drug and enhancers in said reservoir; and
   (5) an adhesive layer over said membrane on the outside of said reservoir for contact with skin and through which drug and enhancers permeate, said adhesive layer containing about 10–40% by weight of a plasticizer-type enhancer and being selected to retain its functioning properties therewith, wherein a modulated three-phase drug administration pattern is obtained when said device is contacted with skin, said pattern having:

(i) a first period in which plasma levels of said drug or a metabolite thereof are obtained, wherein said first period begins at patch application and ends at about two to ten hours after patch application;

(ii) a second period in which therapeutic plasma levels of said drug or a metabolite thereof are maintained, wherein said second period begins at about two to ten hours after patch application and ends at about eight to eighteen hours after patch application; and (iii) a third period in which sub-therapeutic plasma levels of said drug or a metabolite thereof are maintained, wherein said third period begins at about eight to eighteen hours after patch application; and (b) administering the drug to the skin in a therapeutically effective amount by permeation of the drug from the reservoir through said membrane and adhesive layer onto the skin.

27. The method of claim 26, wherein said drug is a tolerance-inducing drug.

28. The method of claim 27, wherein said tolerance-inducing drug is selected from the group consisting of isosorbide dinitrate, isosorbide 2-mononitrate and isosorbide 5-mononitrate.

29. The method of claim 28, wherein said tolerance-inducing drug comprises isosorbide dinitrate.

30. The method of claim 27, wherein said drug is present in said reservoir in an amount of from about 0.1 to about 70% by weight.

31. The method of claim 30, wherein said drug is present in said reservoir in an amount of from about 0.5 to about 40% by weight.

32. The method of claim 26, wherein said plasticizer-type enhancer in said reservoir is selected from the group consisting of lower alkyl esters of fatty acids, fatty acids, and fatty alcohols.

33. The method of claim 32, wherein said plasticizer-type enhancer in said reservoir comprises a lower alkyl ester of a fatty acid.

34. The method of claim 26, wherein said plasticizer-type enhancer in said reservoir comprises isopropyl myristate.

35. The method of claim 26, wherein said solvent-type enhancer is selected from the group consisting of lower alkyl alcohols, aryl alcohols, and polyols.

36. The method of claim 26, wherein said solvent-type enhancer comprises a lower alkyl alcohol.

37. The method of claim 36, wherein said solvent-type enhancer comprises ethanol.

38. The method of claim 26, wherein the ratio of said plasticizer-type enhancer to said solvent-type enhancer in said reservoir is from about 1 part of plasticizer-type enhancer to at least about 10 parts of solvent-type enhancer.

39. The method of claim 26, wherein the ratio of said plasticizer-type enhancer to said solvent-type enhancer in said reservoir is from about 1 part of plasticizer-type enhancer to at least about 20 parts of solvent-type enhancer.

40. The method of claim 26, wherein said plasticizer-type enhancer in said adhesive layer is selected from the group consisting of lower alkyl esters of fatty acids, fatty acids, and fatty alcohols.

41. The method of claim 40, wherein said plasticizer-type enhancer in said adhesive layer comprises isopropyl myristate.

42. The method of claim 26, wherein said plasticizer-type enhancer in said adhesive layer is present in an amount from about 25 to about 35% by weight.

43. The method of claim 26, wherein said adhesive layer comprises a cross-linked acrylate-based adhesive.

44. The method of claim 26, wherein said membrane has a pore size diameter between about 0.08 and 0.5 microns.

* * * * *